US007524826B2

(12) United States Patent
Austin et al.

(10) Patent No.: US 7,524,826 B2
(45) Date of Patent: Apr. 28, 2009

(54) METHOD OF INHIBITING THE GENERATION OF ACTIVE THROMBIN ON THE SURFACE OF A CELL WITHIN AN ATHEROSCLEROTIC PLAQUE

(75) Inventors: Richard C. Austin, Ancaster (CA); Anthony K. C. Chan, Ancaster (CA); Leslie Roy Berry, Burlington (CA)

(73) Assignee: McMaster University and Hamilton Health Sciences Corporation, Hamilton (CA)

( * ) Notice: Subject to any disclaimer, the term of this patent is extended or adjusted under 35 U.S.C. 154(b) by 0 days.

(21) Appl. No.: 09/834,760

(22) Filed: Apr. 12, 2001

(65) Prior Publication Data

US 2002/0039791 A1    Apr. 4, 2002

Related U.S. Application Data

(60) Provisional application No. 60/197,146, filed on Apr. 14, 2000.

(51) Int. Cl.
*A61K 31/70* (2006.01)
(52) U.S. Cl. ...................................................... 514/44
(58) Field of Classification Search ................ 435/69.1; 514/44
See application file for complete search history.

(56) References Cited

U.S. PATENT DOCUMENTS 5,208,019 A * 5/1993 Hansson et al. ............ 424/85.5

OTHER PUBLICATIONS

W Walther et al.,Drugs, "Viral Vectors for Gene Transfer," Aug. 2000, 60(2):249-271.*
IM Verma et al., Nature, "Gene therapy-promises, problems and prospects," Sep. 1997, vol. 389, pp. 239-242.*
RG Crystal, Science, "Transfer of Genes to Humans: Early Lessons and Obstacles to Success," Oct. 1995, vol. 270, pp. 404-410.*
A Nakai et al., Cell Structure and Function, "Expression and Phosphorylation of BiP/GRP78, a Molecular Chaperone in the Endoplasmic Reticulum, during the Differentiation of a Mouse Myeloblastic Cell Line," 1995, 20: 33-39.*
M Cheng et al., Int.J. Exp.Path., "Expression of the heat shock protein 47 in gentamicin-treated rat kidneys," 1998, 79, 125-132.*
Anderson W.F. Human gene therapy. Nature 1998; 392(suppl):25-30.*
Greco O. et al. Cancer gene therapy, 'delivery, delivery, delivery'. Frontiers in Biosci. 2002; 7:d1516-1524.*
Mallat et al. Protective role of Interleukin-10 in atherosclerosis. Circulation Research 1999; vol. 85:e17-e24.*
Dai et al. calreticulin, a potential vascular regulatory protein, reduces intimal hyperplasia after arterial injury. Arteriosclerosis, Thrombosis, Vascular Biology 1997; vol. 17, pp. 2359-2368.*
Sauk et al. (Frontiers in Bioscience, vol. 10, 2005; pp. 107-118).*
Shou et al. (Nature, vol. 391, 1998; pp. 489-492).*
Vannucchi et al. (Haematologica, vol. 80, 1995; pp. 341-343).*
Brewer, et al., "A pathway distinct from the mammalian unfolded protein response regulates expression of endoplasmic reticulum chaperones in non-stressed cells," *EMBO J.*, 16(23):7207-7216 (1997).

Chan, et al., "Effect of a novel covalent antithrombin-heparin complex on thrombin generation on fetal distal lung epithelium," *Lung Cell. Mol. Physiol.*, 18:L914-L921 (1998).
Ellis, et al., "Molecular chaperones: proteins essential for the biogenesis of some macromolecular structures," *Trends Biochem. Sci.*, 14(8):339-42 (1989).
Fliegel, et al., "Molecular cloning of the high affinity calcium-binding protein (calreticulin) of skeletal muscle sarcoplasmic reticulum," *J. Biol. Chem.*, 264(36):21522-8 (1989).
Kozutsumi, et al., "Identification of immunoglobulin heavy chain binding protein as glucose-regulated protein 78 on the basis of amino acid sequence, immunological cross-reactivity, and functional activity," *J. Cell Sci. Suppl.*, 11:115-37 (1989).
Ling, et al., "$\alpha_2$-Macroglobulin remains as important as antithrombin III for thrombin regulation in cord plasma in the presence of endothelial cell surfaces," *Pediatr. Res.*, 37(3):373-378 (1995).
Liu, et al., "Endoplasmic reticulum chaperones GRP78 and calreticulin prevent oxidative stress, $Ca^{2+}$ disturbances, and cell death in renal epithelial cells," *J. Biol. Chem.*, 272(35):21751-21759 (1997).
Liu, et al., "Endoplasmic reticulum stress proteins block oxidant-induced $Ca^{2+}$ increases and cell death," *J. Biol. Chem.*, 273(21):12858-12862 (1998).
Michalak, et al., "Calreticulin," *Biochem. J.*, 285:681-92 (1992).
Morris, et al., "Immunoglobulin binding protein (BiP) function is required to protect cells from endoplasmic reticulum stress but is not required for the secretion of selective proteins," *J. Biol. Chem.*, 272(7):4327-34 (1997).
Outinen, et al., "Characterization of the stress-inducing effects of homocysteine," *Biochem. J.*, 332:213-221 (1998).
Outinen, et al., "Homocysteine-induced endoplasmic reticulum stress and growth arrest leads to specific changes in gene expression in human vascular endothelial cells," *Blood*, 94(3):959-967 (1999).
Ozawa, et al., "Reticulocalbin, a novel endoplasmic reticulum Resident $Ca^{2+}$-binding protein with multiple EF-hand motifs and a carboxyl-terminal HDEL sequence," *J. Biol. Chem.*, 268(2):699-705 (1993).
Penn, et al., "Hydrogen peroxide activates latent cell surface tissue factor," *Circulation*, 99:1753-1759 (1999).
Ruddon, et al., "Assisted protein folding," *J. Biol. Chem.*, 272(6):3125-3128 (1997).
Sorger, et al., "The glucose-regulated protein grp94 is related to heat shock protein hsp90," *J. Mol. Biol.*, 194:341-4 (1987).
Ting, et al., "Human gene encoding the 78,000-Dalton glucose-regulated protein and its pseudogene: structure, conservation, and regulation," *DNA*, 7(4):275-86 (1988).
Wada, et al., "SSR$\alpha$ and associated calnexin are major calcium binding proteins of the endoplasmic reticulum membrane," *J. Biol. Chem.*, 266(29):19599-19610 (1991).

* cited by examiner

*Primary Examiner*—J. E Angell
(74) *Attorney, Agent, or Firm*—Townsend and Townsend and Crew LLP

(57) ABSTRACT

The present invention provides methods for preventing the generation of active thrombin on the surface of cells. The present methods are based upon the surprising discovery that expression or activation of an ER resident chaperone protein in a cell inhibits the generation of thrombin on the surface of the cell. Accordingly, expressing or activating an ER resident chaperone protein can be used to treat or prevent any of a number of thrombotic diseases.

10 Claims, 7 Drawing Sheets
(2 of 7 Drawing Sheet(s) Filed in Color)

wild-type T24/83

T24/83-GRP78c1

A

B

SEQUENCE LISTING

<160> NUMBER OF SEQ ID NOS: 5

<210> SEQ ID NO 1
<211> LENGTH: 24

```
<212> TYPE: DNA
<213> ORGANISM: Artificial Sequence
<220> FEATURE:
<223> OTHER INFORMATION: Description of Artificial Sequence: Primer
      AB10230

<400> SEQUENCE: 1
tattacagca ctagcagatc agtg                                            24

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Primer
      AB10231

<400> SEQUENCE: 2
cttaagcttg ccaccatgaa gctctccctg gtggccgcg                            39

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Primer
      AB10232

<400> SEQUENCE: 3
aggcctcgag ctacaactca tcttttctg ctgt                                  34

<210> SEQ ID NO 4
<211> LENGTH: 654
<212> TYPE: PRT
<213> ORGANISM: Homo sapiens
<220> FEATURE:
<223> OTHER INFORMATION: GRP78/BiP amino acid sequence

<400> SEQUENCE: 4

Met Lys Leu Ser Leu Val Ala Ala Met Leu Leu Leu Leu Ser Ala Ala
  1               5                  10                  15

Arg Ala Glu Glu Glu Asp Lys Lys Glu Asp Val Gly Thr Val Val Gly
                 20                  25                  30

Ile Asp Leu Gly Thr Thr Tyr Ser Cys Val Gly Val Phe Lys Asn Gly
             35                  40                  45

Arg Val Glu Ile Ile Ala Asn Asp Gln Gly Asn Arg Ile Thr Pro Ser
         50                  55                  60

Tyr Val Ala Phe Thr Pro Glu Gly Glu Arg Leu Ile Gly Asp Ala Ala
 65                  70                  75                  80

Lys Asn Gln Leu Thr Ser Asn Pro Glu Asn Thr Val Phe Asp Ala Lys
                 85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175
```

-continued

```
Asn Asp Ala Gln Arg Gln Ala Thr Lys Asp Ala Gly Thr Ile Ala Gly
            180                 185                 190
Leu Asn Val Met Arg Ile Ile Asn Glu Pro Thr Ala Ala Ala Ile Ala
        195                 200                 205
Tyr Gly Leu Asp Lys Arg Glu Gly Glu Lys Asn Ile Leu Val Phe Asp
    210                 215                 220
Leu Gly Gly Gly Thr Phe Asp Val Ser Leu Leu Thr Ile Asp Asn Gly
225                 230                 235                 240
Val Phe Glu Val Val Ala Thr Asn Gly Asp Thr His Leu Gly Gly Glu
                245                 250                 255
Asp Phe Asp Gln Arg Val Met Glu His Phe Ile Lys Leu Tyr Lys Lys
            260                 265                 270
Lys Thr Gly Lys Asp Val Arg Lys Asp Asn Arg Ala Val Gln Lys Leu
        275                 280                 285
Arg Arg Glu Val Glu Lys Ala Lys Arg Ala Leu Ser Ser Gln His Gln
    290                 295                 300
Ala Arg Ile Glu Ile Glu Ser Phe Tyr Glu Gly Glu Asp Phe Ser Glu
305                 310                 315                 320
Thr Leu Thr Arg Ala Lys Phe Glu Glu Leu Asn Met Asp Leu Phe Arg
                325                 330                 335
Ser Thr Met Lys Pro Val Gln Lys Val Leu Glu Asp Ser Asp Leu Lys
            340                 345                 350
Lys Ser Asp Ile Asp Glu Ile Val Leu Val Gly Gly Ser Thr Arg Ile
        355                 360                 365
Pro Lys Ile Gln Gln Leu Val Lys Glu Phe Phe Asn Gly Lys Glu Pro
    370                 375                 380
Ser Arg Gly Ile Asn Pro Asp Glu Ala Val Ala Tyr Gly Ala Ala Val
385                 390                 395                 400
Gln Ala Gly Val Leu Ser Gly Asp Gln Asp Thr Gly Asp Leu Val Leu
                405                 410                 415
Leu Asp Val Cys Pro Leu Thr Leu Gly Ile Glu Thr Val Gly Gly Val
            420                 425                 430
Met Thr Lys Leu Ile Pro Arg Asn Thr Val Val Pro Thr Lys Lys Ser
        435                 440                 445
Gln Ile Phe Ser Thr Ala Ser Asp Asn Gln Pro Thr Val Thr Ile Lys
    450                 455                 460
Val Tyr Glu Gly Glu Arg Pro Leu Thr Lys Asp Asn His Leu Leu Gly
465                 470                 475                 480
Thr Phe Asp Leu Thr Gly Ile Pro Pro Ala Pro Arg Gly Val Pro Gln
                485                 490                 495
Ile Glu Val Thr Phe Glu Ile Asp Val Asn Gly Ile Leu Arg Val Thr
            500                 505                 510
Ala Glu Asp Lys Gly Thr Gly Asn Lys Asn Lys Ile Thr Ile Thr Asn
        515                 520                 525
Asp Gln Asn Arg Leu Thr Pro Glu Glu Ile Glu Arg Met Val Asn Asp
    530                 535                 540
Ala Glu Lys Phe Ala Glu Asp Lys Lys Leu Lys Glu Arg Ile Asp
545                 550                 555                 560
Thr Arg Asn Glu Leu Glu Ser Tyr Ala Tyr Ser Leu Lys Asn Gln Ile
                565                 570                 575
Gly Asp Lys Glu Lys Leu Gly Gly Lys Leu Ser Ser Glu Asp Lys Glu
            580                 585                 590
Thr Met Glu Lys Ala Val Glu Glu Lys Ile Glu Trp Leu Glu Ser His
```

```
              595                 600                 605
Gln Asp Ala Asp Ile Glu Asp Phe Lys Ala Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 5
<211> LENGTH: 2007
<212> TYPE: DNA
<213> ORGANISM: Homo sapiens
<220> FEATURE:
<223> OTHER INFORMATION: Human GRP78/BiP mRNA   sequence

<400> SEQUENCE: 5
actggctggc aagatgaagc tctccctggt ggccgcgatg ctgctgctgc tcagcgcggc      60
gcgggccgag gaggaggaca agaaggagga cgtgggcacg gtggtcggca tcgacctggg     120
gaccacctac tcctgcgtcg gcgtgttcaa gaacggccgc gtggagatca tcgccaacga     180
tcagggcaac cgcatcacgc cgtcctatgt cgccttcact cctgaagggg aacgtctgat     240
tggcgatgcc gccaagaacc agctcacctc caaccccgag aacacggtct ttgacgccaa     300
gcggctcatc ggccgcacgt ggaatgaccc gtctgtgcag caggacatca gttcttgcc      360 gttcaaggtg gttgaaaaga aaactaaacc atacattcaa gttgatattg gaggtgggca     420
aacaaagaca tttgctcctg aagaaatttc tgccatggtt ctcactaaaa tgaaagaaac     480
cgctgaggct tatttgggaa agaaggttac ccatgcagtt gttactgtac agcctatttt     540
taatgatgcc aacgccaag caaccaaaga cgctggaact attgctggcc taaatgttat     600
gaggatcatc aacgagccta cggcagctgc tattgcttat ggcctggata gagggaggg      660 ggagaagaac atcctggtgt tgacctgggt ggcggaacc ttcgatgtgt ctcttctcac      720
cattgacaat ggtgtcttcg aagttgtggc cactaatgga gatactcatc tgggtggaga     780
agactttgac cagcgtgtca tggaacactt catcaaactg tacaaaaaga gacgggcaa      840 agatgtcagg aaagacaata gagctgtgca gaaactccgg cgcgaggtag aaaaggccaa     900
acgggccctg tcttctcagc atcaagcaag aattgaaatt gagtccttct atgaaggaga     960 agactttttct gagaccctga ctcgggccaa atttgaagag ctcaacatgg atctgttccg    1020
gtctactatg aagcccgtcc agaaagtgtt ggaagattct gatttgaaga agtctgatat    1080
tgatgaaatt gttcttgttg gtggctcgac tcgaattcca aagattcagc aactggttaa    1140
agagttcttc aatggcaagg aaccatcccg tggcataaac ccagatgaag ctgtagcgta    1200
tggtgctgct gtccaggctg gtgtgctctc tggtgatcaa gatacaggtg acctggtact    1260
gcttgatgta tgtcccctta cacttggtat tgaaactgtg ggaggtgtca tgaccaaact    1320
gattccaagg aacacagtgg tgcctaccaa gaagtctcag atcttttcta cagcttctga    1380
taatcaacca actgttacaa tcaaggtcta tgaaggtgaa agaccctga caaaagacaa     1440 tcatctcctg ggtacatttg atctgactgg aattcctcct gctcctcgtg ggtcccaca     1500 gattgaagtc acctttgaga tagatgtgaa tggtattctt cgagtgacag ctgaagacaa    1560
gggtacaggg aacaaaaata agatcacaat caccaatgac cagaatcgcc tgacacctga    1620
agaaatcgaa aggatggtta tgatgctga aagtttgct gaggaagaca aaaagctcaa     1680
ggagcgcatt gatactagaa atgagttgga aagctatgcc tattctctaa agaatcagat    1740
```

```
tggagataaa gaaaagctgg gaggtaaact ttcctctgaa gataaggaga ccatggaaaa    1800
agctgtagaa gaaaagattg aatggctgga aagccaccaa gatgctgaca ttgaagactt    1860
caaagctaag aagaaggaac tggaagaaat tgttcaacca attatcagca aactctatgg    1920
aagtgcaggc cctcccccaa ctggtgaaga ggatacagca gaaaaagatg agttgtagac    1980
actgatctgc tagtgctgta atattgt                                        2007
```

METHOD OF INHIBITING THE GENERATION OF ACTIVE THROMBIN ON THE SURFACE OF A CELL WITHIN AN ATHEROSCLEROTIC PLAQUE

CROSS-REFERENCE TO RELATED APPLICATIONS

This application claims benefit of U.S. Provisional Application No. 60/197,146, filed Apr. 14, 2000, which application is incorporated herein by reference for all purposes.

BACKGROUND OF THE INVENTION

Regulation of coagulation is essential for animal survival: deficiencies in coagulation, such as those associated with hemophilia, can produce life-threatening hemorrhage events, whereas excessive coagulation can lead to the formation of dangerous blood clots or can contribute to deleterious processes such as atherosclerosis. Clearly, the ability to modulate the extent of coagulation in cells, e.g., in endothelial cells, within a patient would provide a powerful tool for the treatment or prevention of a large number of common human diseases and conditions.

One key, rate limiting factor in the coagulation pathway is the generation of active thrombin. Indeed, tissue factor (TF)-dependent thrombin generation plays a critical role in hemostasis after tissue injury and also in the pathogenesis of multiple thrombotic disorders associated with a wide range of diseases, including cardiovascular disease, sepsis, and cancer. Accordingly, regulation of thrombin is critical for the prevention of thromboembolic disease and is dependent on an intricate balance between coagulation factors and inhibitors present in plasma and on the surface of cells. Thrombin generation in vivo occurs predominantly on cell surfaces and involves the interaction of tissue factor (TF), an integral membrane glycoprotein, with factor VII/VIIa to initiate blood coagulation. TF is present on the cell surface of lipid-laden macrophages (foam cells) and smooth muscle cells within human atherosclerotic plaques, and contributes to the thrombogenicity of the ruptured plaque. The generation of thrombin is subsequently regulated at the cell surface by thrombomodulin (TM), a cell surface receptor which promotes thrombin-dependent activation of the anticoagulant protein C pathway. Alterations in cell surface levels and/or activity of TF or TM can enhance thrombin generation, thereby increasing the risk of thromboembolic disease. Accordingly, a decrease in TF levels or activity, or an increase in TM levels or activity, would decrease the potential for thrombosis.

The biosynthesis and maturation of TF and TM, as well as other coagulation factors and inhibitors, occurs within the cellular secretory pathway which consists of the ER, Golgi complex and a variety of intermediate transport vesicles. The ER is the cellular organelle where these factors and inhibitors undergo a series of modifications, including folding, proteolytic processing, glycosylation, disulfide-bond formation and oligomeric assembly. Failure to fold properly or to assemble into correct oligomeric complexes can result in the generation of dysfunctional molecules and/or the retention of these molecules in the ER, followed by degradation.

To assist in the proper folding and assembly of newly synthesized proteins, the ER lumen contains a number of molecular chaperones, including GRP78/BiP, the 94 kDa glucose-regulated protein (GRP94), Calnexin, Calreticulin and ERp72. These molecular chaperones are important components of the quality control system of the ER that allows export of correctly folded and assembled proteins.

Overexpression of GRP78/BiP in cultured mammalian cells can affect the processing and secretion of several coagulation and fibrinolytic factors, including von Willebrand factor (vWf), factor VIII and tissue plasminogen activator (tPA). Recent studies using cultured human vascular endothelial cells have also shown that homocysteine, a thiol-containing amino acid implicated in the progression of atherothrombosis, induces the expression of GRP78/BiP while decreasing the processing and secretion of vWf.

SUMMARY OF THE INVENTION

The present invention provides novel methods for inhibiting thrombin on the surface of cells. This invention is based on the surprising discovery that the expression or activation of an ER resident chaperone in a cell prevents the generation of thrombin on the cell surface. As thrombin is the rate-limiting factor in coagulation, this invention thus provides methods for inhibiting coagulation, thereby providing a treatment for any of a number of thrombotic diseases and conditions.

Thus, in one aspect, the present invention provides a method of inhibiting the generation of active thrombin on the surface of a cell of a mammal, the method comprising producing an ER resident chaperone protein in the cell.

In one embodiment, the cell is an endothelial cell. In another embodiment, the cell is a smooth muscle cell. In another embodiment, the cell is a macrophage. In another embodiment, the cell is a monocyte. In another embodiment, the ER resident chaperone protein is GRP78/BiP. In another embodiment, the ER resident chaperone protein is selected from the group consisting of GRP94, GRP72, Calreticulin, Calnexin, Protein disulfide isomerase, cis/trans-Prolyl isomerase, and HSP47. In another embodiment, the production of the ER resident chaperone protein within the cell results in a decrease in the level of tissue factor activity on the surface of the cell.

In another embodiment, the cell is present within the mammal. In another embodiment, the cell is present within an atherosclerotic plaque in the mammal. In another embodiment, a polynucleotide encoding the ER resident chaperone, operably linked to a promoter, is introduced into the cell, whereby the ER resident chaperone protein is produced. In another embodiment, the polynucleotide is introduced into the cell using a viral vector. In another embodiment, the viral vector is an adenoviral vector. In another embodiment, the polynucleotide is introduced into the cell using a nonviral vector. In another embodiment, the nonviral vector is introduced into the cell as naked DNA or using liposome-mediated transfection. In another embodiment, the ER resident chaperone protein is produced by administering to the cell a compound that induces the expression or activation of an endogenous ER resident chaperone protein. In another embodiment, the compound is a cytokine.

In another aspect, the present invention provides a method of preventing or treating a thrombotic disease or condition in a mammal, the method comprising producing an ER resident chaperone protein within a population of cells of the mammal, whereby the generation of thrombin on the surface of the cells is inhibited.

In one embodiment, the population of cells comprises endothelial cells. In another embodiment, the population of cells comprises smooth muscle cells. In another embodiment, the population of cells comprises macrophages. In another embodiment, the cells comprise monocytes. In another embodiment, the ER resident chaperone protein is GRP78/BiP. In another embodiment, the ER resident chaperone protein is selected from the group consisting of GRP94, GRP72, Calreticulin, Calnexin, Protein disulfide isomerase, cis/trans-Prolyl isomerase, and HSP47. In another embodiment, the production of the ER resident chaperone protein within the population of cells results in a decrease in the level of tissue factor activity on the surface of the population of cells. In another embodiment, the population of cells is present within an atherosclerotic plaque within the mammal.

In another embodiment, the mammal has had a myocardial infarction and is undergoing angioplasty or stenting, and the inhibition of the generation of thrombin on the surface of the population of cells reduces the risk of thrombosis of the mammal during the angioplasty or stenting. In another embodiment, the mammal is undergoing stenting and the population of cells is present on the surface of a stent. In another embodiment, the mammal is undergoing cranial radiation, and the inhibition of the generation of thrombin on the surface of the population of cells reduces the risk of radiation-related thrombotic events during the cranial radiation. In another embodiment, the mammal is undergoing vascular surgery, and the inhibition of the generation of thrombin on the surface of the population of cells reduces the risk of surgery-related thrombotic events during the vascular surgery.

In another embodiment, a polynucleotide encoding the ER resident chaperone protein, operably linked to a promoter, is introduced into the population of cells, whereby the ER resident chaperone protein is produced. In another embodiment, the polynucleotide is introduced into the population of cells using a viral vector. In another embodiment, the viral vector is an adenoviral vector. In another embodiment, the polynucleotide is introduced into the population of cells using a nonviral vector. In another embodiment, the nonviral vector is introduced into the cell as naked DNA or using liposome-mediated transfection. In another embodiment, the ER resident chaperone protein is produced by administering to the population of cells a compound that induces the expression or activation of an endogenous ER resident chaperone protein. In another embodiment, the compound is a cytokine.

In another aspect, the present invention provides a method of identifying a compound that is useful in the treatment or prevention of a thrombotic disease or condition, the method comprising (1) contacting a cell that expresses an ER resident chaperone protein, or that is capable of expressing an ER resident chaperone protein; and (2) detecting the functional effect of the compound on the ER resident chaperone protein; wherein an increase in the expression or activity of the ER resident chaperone protein in the cell indicates that the compound would be useful in the treatment or prevention of the thrombotic disease or condition.

In one embodiment, the ER resident protein is GRP78/BiP. In another embodiment, the ER resident protein is selected from the group consisting of GRP94, GRP72, Calreticulin, Calnexin, Protein disulfide isomerase, cis/trans-Prolyl isomerase, and HSP47. In another embodiment, the cell is an endothelial cell. In another embodiment, the cell is a smooth muscle cell. In another embodiment, the cell is a macrophage. In another embodiment, the cell is a monocyte. In another embodiment, the compound induces the expression or activation of the ER resident chaperone protein in the cell without inducing ER stress in the cell.

In another aspect, the present invention provides a method of treating or preventing a thrombotic disease in a mammal, the method comprising administering to the mammal a therapeutically or prophylactically effective amount of a compound identified using a method comprising (1) contacting a cell that expresses an ER resident chaperone protein, or that is capable of expressing an ER resident chaperone protein; and (2) detecting the functional effect of the compound on the ER resident chaperone protein; wherein an increase in the expression or activity of the ER resident chaperone protein in the cell indicates that the compound would be useful in the treatment or prevention of the thrombotic disease or condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

83 cells (T24/83-GRP78) using a radiolabeled human TF cDNA probe. The migration position of TF mRNA is shown by the arrowhead. To control for RNA loading, blots were hybridized with a radiolabeled GAPDII cDNA probe (lower panel). (B) Immunoblot analysis of total protein lysates (30 μg/lane) from wild-type (T24/83), vector-transfected (T24/83-pcDNA) or GRP78/BiP overexpressing T24/83 cells (T24/83-GRP78). Lysates were separated by SDS-polyacrylamide gel electrophoresis under reducing conditions and gels were either stained with Coomassie Blue (upper panel) or immunostained with an anti-human TF mAb (lower panel). The migration position of TF is shown by the arrowhead. The asterisk indicates the migration position of GRP78/BiP, which is increased in lane 3.

Figure 7:
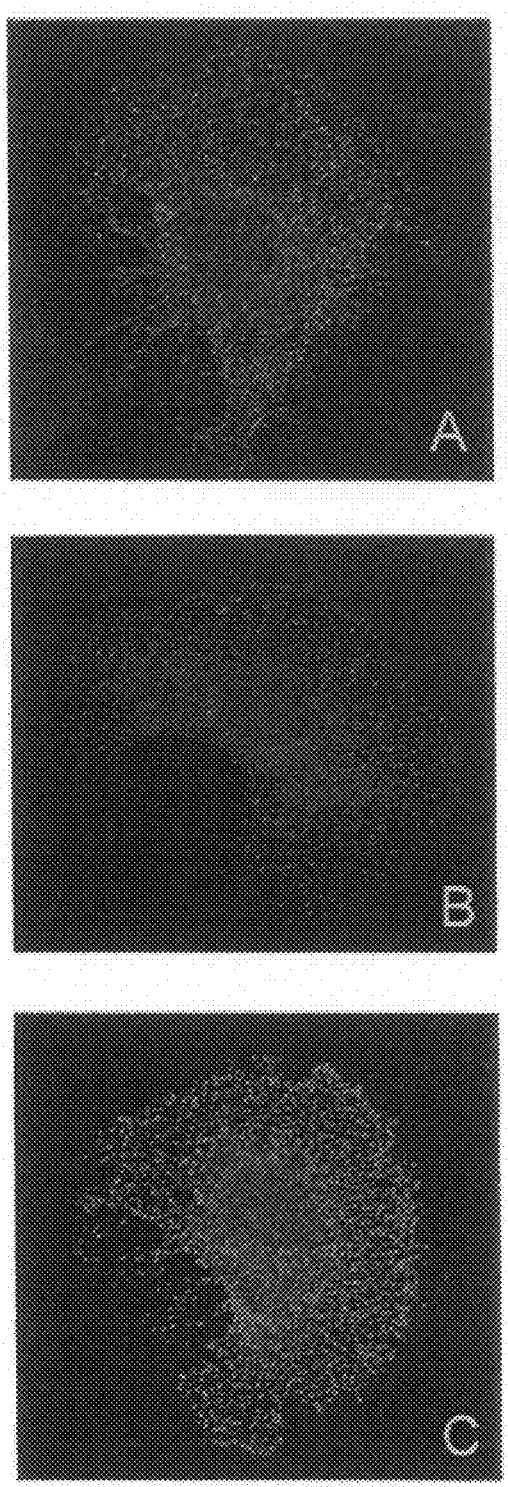

FIG. 7. Increased cell surface levels of TF in GRP78/BiP overexpressing cells. Wild type (A), vector-transfected (B) or GRP78/BiP overexpressing T24/83 cells (C) were grown on coverslips and incubated for 1 hr at 4° C. with an anti-human TF mAb. Following incubation with a goat Alexa-conjugated anti-mouse IgG, cells were fixed in 1% paraformaldehyde. Magnification ×1000.

DETAILED DESCRIPTION OF THE INVENTION AND PREFERRED EMBODIMENTS

I. Introduction

The present invention provides novel methods for preventing the tissue-factor dependent generation of thrombin on the surface of cells. These methods are based upon the surprising discovery that the expression or activation of an ER resident chaperone protein in a cell inhibits the generation of thrombin on the surface of the cell, and that this inhibition occurs in conjunction with a decrease in the level of prothrombin consumption, tissue factor procoagulant activity, and thrombin-inhibitor complexes. Accordingly, expressing or activating an ER resident chaperone protein in a cell can be used to inhibit coagulation in the vicinity of the cell, thereby providing a method for the treatment or prevention of any of a number of thromboembolic conditions and diseases. In addition to inhibiting thrombin generation, the overexpression of ER resident chaperone proteins can also be used to decrease tissue factor (TF) procoagulant activity (PCA), cell-surface-mediated prothrombin consumption, or the formation of thrombin-inhibitor complexes. In addition to these effects, ER resident chaperones such as GRP78/BiP also protect the cells from oxidative and ER stress. Thus, cells expressing the chaperones will also be resistant to physiological perturbants known to cause cell injury or dysfunction.

In numerous embodiments of this invention, the expression of an ER resident chaperone protein, such as GRP78/BiP, is induced in a population of cells of a mammal. The expression or activity of such proteins can be induced in any of a number of ways, including by introducing a polynucleotide encoding the chaperone protein into the cells or by introducing into the cells a polynucleotide that encodes a protein that induces the chaperone protein. Alternatively, the cells can be treated with compounds, such as proteins or small molecules, that induce the activity or expression of these proteins.

Without being bound by the presently offered theories, it is hypothesized that, at least in part, the effect of ER resident chaperones such as GRP78/BiP on the generation of active thrombin on the surface of cells is mediated by TF, i.e. the expression of the chaperones inhibits the generation of active TF on the surface of the cells, thereby preventing the conversion of prothrombin to thrombin. Accordingly, the present methods are particularly useful in the prevention of the generation or accumulation of active thrombin on the surface of TF-expressing cells. It is further speculated that the effect of the chaperones such as GRP78/BiP on TF and thrombin may be mediated by calcium, i.e. overexpression of the calcium-binding GRP78/BiP causes a reduction in the level of available calcium within the ER, thereby preventing the production of active TF on the cell surface. As a result, the generation of active thrombin on the cell surface is inhibited. Accordingly, thrombin can be inhibited in the surface of cells by the application of any treatment or compound that causes a decrease in the level of free calcium in the ER, such as the expression of ER resident calcium binding proteins such as Calreticulin or Calretuxin.

Other possible mechanisms for the observed effect include a conformational change in TF quaternary structure, thereby decreasing its procoagulant activity (PCA), or a modulation of the accessibility of anionic phospholipid essential for TF PCA. Another possible mechanism follows from recent studies using smooth muscle cells that have shown that LDL increases steady-state levels of TF mRNA and cell surface protein, but does not affect TF PCA (Penn et al., (1999) *Circulation* 99:1753-1759), and that hydrogen peroxide stimulates TF activity on the cell surface but does not increase TF mRNA or cell surface protein. These findings support a 2-step activation pathway for increased TF activity in which lipoproteins (or other cellular factors) regulate synthesis of latent TF while oxidants mediate post-translational modifications that enhance cell surface TF PCA. Given that GRP78/BiP prevents oxidant-induced cell dysfunction/injury (see, e.g., Liu et al., (1997) *J. Biol. Chem.* 272:21751-21759; Liu et al., (1998) *J. Biol. Chem.* 273:12858-12862; Morris et al., (1997) *J. Biol. Chem.* 272:4327-4334), it is possible that overexpression of GRP78/BiP inhibits the oxidant-dependent activation of latent TF at the cell surface.

It is also speculated that the effect of ER chaperones on thrombin generation is mediated by thrombomodulin (TM), which promotes thrombin-dependent activation of the anti-coagulant protein C (APC) pathway, i.e., an increase in the level of an ER chaperone causes an increase in the level of TM on the cell surface, thereby causing a decrease in thrombin activity on the cell surface. Accordingly, the present methods are particularly useful in the prevention of the accumulation of active thrombin on the surface of TM-expressing cells.

The present invention also provides methods for identifying compounds useful in the treatment or prevention of thromboembolic diseases and conditions. In numerous embodiments, these methods involve contacting a cell with a test agent, wherein the cell either expresses, or is capable of expressing, an ER resident chaperone protein, and determining the effect of the test agent on the level of expression or activity of the ER resident chaperone in the cell. In other embodiments, the methods involve contacting an ER resident chaperone protein with a test agent, and determining the effect of the test agent on the activity of the ER resident chaperone protein. In each of these methods, a compound that is found to increase the level or activity of the ER resident chaperone represents a candidate for a compound useful in the treatment or prevention of thromboembolic diseases and conditions.

It will be appreciated that the herein-described relationship between ER resident chaperones is valid in either direction, i.e. an increase in the level or activity of an ER resident chaperone can be used to decrease the level of active thrombin or TF on the surface of cells, and a decrease in the ER resident chaperone can be used to increase the level of active thrombin or TF on the cell surface.

The inhibition of thrombin generation on the surface of cells can be used to prevent or treat any of a number of thrombotic or other cardiovascular diseases or conditions. For example, as intravascular coagulation is associated with atherosclerosis, myocardial infarction, and acute arterial thrombosis following plaque disruption, the present methods can be used to prevent or treat any of these conditions or diseases. In addition, as TF-induced thrombin generation plays a critical role in hemostasis following tissue injury and also in the pathogenesis of multiple thrombotic disorders associated with a wide range of diseases including, but not limited to, cardiovascular disease, sepsis, and cancer, the present methods can also be used to treat or prevent these diseases and conditions. The level of an ER resident chaperone can thus be used to prevent thrombin accumulation on the surface of cells in the endothelium of patients who have had a myocardial infarction and who are undergoing angioplasty or stenting, thereby reducing the risk of thrombosis. In addition, the level can be increased in the endothelium of patients undergoing cranial radiation to prevent radiation-related thrombotic events. In addition, the level of ER resident chaperone protein or protein activity can be increased in the endothelium of patients undergoing vascular surgery to prevent surgery related thrombosis.

In addition, the present invention provides methods for using cells, such as the endothelial cell lines overexpressing GRP78/BiP, as model systems to better understand the factors which mediate cell surface thrombin generation in endothelial cells.

The therapeutic and prophylactic methods of this invention can be used in any mammal, including, but not limited to, humans and other primates, canines, felines, murines, bovines, equines, ovines, porcines, and lagomorphs.

Kits are also provided for carrying out the herein-disclosed diagnostic and therapeutic methods.

II. Definitions

An "ER resident chaperone protein" refers to any protein, present in, or associated with, the ER, that acts to facilitate the folding, assembly, or translocation of proteins (see, e.g., Ellis et al., (1989) *Trends Biochem Sci* 14(8):339-42; Ruddon et al., (1997) *J. Biol. Chem.* 272:3125-3128). As used herein, "ER resident chaperone proteins" can refer to any protein that facilitates protein folding, assembly, or translocation, and which is naturally present in the ER or which is modified to be present in the ER, for example by the recombinant addition of a signal sequence and/or other ER localization domains. Examples of ER resident chaperone proteins include, but are not limited to, BiP/GRP78 (see, e.g., GenBank accession No. AJ271729; see, also, SEQ ID NOs: 1 and 2), GRP94, GRP72, Calreticulin, Calnexin (p88, IP90), TRAP or p28, cis/trans-Prolyl isomerase, Protein disulfide isomerase, and others (see, e.g., Ruddon et al., supra). The term "ER resident chaperone protein" also refers to any variant or derivative of any of the above proteins.

The "ER," or "endoplasmic reticulum," refers to a highly convoluted membrane, present in nearly every eukaryotic cell, that is organized into a netlike meshwork that extends throughout the cytoplasm. Transmembrane and secreted proteins are synthesized in association with the ER membrane, and proteins destined to remain in the ER lumen, the Golgi apparatus, or lysosomes are at least initially delivered to the ER lumen, the internal space enclosed by the ER membrane. The ER is also involved in the synthesis of lipids, including those used to form membranes such as the plasma, mitochondrial, and peroxisomal membranes. The ER is also the site of numerous modifications to secreted or membrane associated proteins, including secreted coagulation factors such as TF and TM; such modifications include folding, proteolytic processing, glycosylation, disulphide-bond formation, and oligomeric assembly. The ER comprises two types of endoplasmic reticulum, called "rough ER" and "smooth ER." The rough ER corresponds to regions of the ER in which proteins are synthesized and immediately translocated across the membrane. The ER membrane in such regions are dotted with ribosomes, giving it a "rough" appearance. The smooth ER corresponds to regions of the ER that lack bound ribosomes. As used herein, "ER" refers to rough ER, smooth ER, as well as transitional elements that include partly rough and partly smooth regions. A factor that is said to be "in" or "associated with" the ER refers to any factor that is permanently, transiently, and/or inducibly located in the ER lumen, in the ER membrane, or associated with the ER membrane, e.g., a cytosolic protein in close proximity to the ER membrane.

"Control cells," in the context of an assay, refers to a population of cells grown under standard conditions, i.e., in the absence of a test agent. The "level" of a protein or mRNA of interest can be measured in such cells expressly for use in the methods described in this invention, or can refer to an established level of, e.g., ER resident chaperone mRNA, protein, or protein activity, which has been previously established based on measurements from untreated cells grown under similar conditions. If a detection method is used that only detects a level of polypeptide or polynucleotide when a level higher than that typical of control cells is present, i.e., an immunohistochemical assay giving a simple positive or negative result, this is considered to be assessing the level of the polypeptide or polynucleotide in comparison to the control cells, as the level typical of the control cells is inherent in the assay.

An "increased" or "elevated" level of a polypeptide or polynucleotide, e.g., an ER resident chaperone or thrombin, or of a detectable activity of the polypeptide, refers to a level of the polynucleotide or polypeptide, that, in comparison with a control level, is detectably higher. Similarly, a "decreased" level refers to a level that, in comparison with a control level, is detectably lower. The method of comparison can be statistical, using quantified values, or can be compared using non-statistical means, such as by a visual, subjective assessment by a human.

The phrase "functional effects" in the context of assays for testing compounds that modulate ER resident chaperone levels or activity includes the determination of any parameter that is indirectly or directly under the influence of the chaperone, e.g., functional, physical and chemical effects. It includes binding to other proteins or other compounds, changes in TF, TM, or thrombin activity or levels, chaperone phosphorylation or dephosphorylation, the ability to counteract ER stress, or inducers of ER stress such as unfolded proteins, $Ca^{2+}$ levels, and also includes other physiologic effects such as coagulation and associated conditions including atherosclerosis.

An "inducer" or "activator" of an ER resident chaperone refers to any compound, e.g., protein, polynucleotide, small organic or inorganic molecule, that causes a net increase in the level of DNA, RNA, protein, or protein activity of an ER resident chaperone. Such inducers can act, e.g., by increasing the transcription, translation, stability, or protein activity of the chaperone, directly or indirectly, by any mechanism, and in vivo, ex vivo, or in vitro. Inducers include genetically modified versions of ER resident chaperones, e.g., with altered activity, as well as naturally occurring and synthetic small chemical molecules and the like. Such assays for inducers include, e.g., applying putative modulator compounds to a cell that expresses an ER resident chaperone, or that is capable of expressing an ER resident chaperone, and determining the functional effects on the expression or activity of the ER resident chaperone. Samples or assays that are treated with a potential inducer are compared to control samples without the inducer to examine the extent of induction. Control samples (untreated with inhibitors) are assigned a relative value of 100%. Induction of an ER resident chaperone is achieved when the value relative to the control is about 110%, optionally 150%, optionally 200-500%, or 1000-3000% higher.

"Biologically active" ER resident chaperone refers to a chaperone having activity as described herein, in particular regarding the capacity to modulate the accumulation of active thrombin on the surface of cells.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid is separated from open reading frames that flank the gene and which encode heterologous proteins. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

I. Expressing or Activating ER Resident Chaperone Proteins

In numerous embodiments of the present invention, an ER resident chaperone, e.g., GRP78/BiP, is expressed or activated within one or more mammalian cells. Preferably, the cells are present within a mammal, i.e., the methods are in vivo methods, and the cells are associated with an existing, or potential, thromboembolic condition or disease, for example endothelial or macrophage cells (including foam cells) at an atherosclerotic lesion.

Any ER resident chaperone protein can be used in the present methods. In a particularly preferred embodiment, the expression or activity of GRP78/BiP is increased (see, e.g., Kozutsumi et al. (1989) *J Cell Sci Suppl* 11:115-37; Ting et al. (1988) *DNA* 7(4):275-86; GenBank Accession No. M19645). In addition to GRP78/BiP, any other ER resident chaperone protein, such as GRP94 (see, e.g., Sorger et al. (1987) *J Mol Biol* 194(2):341-4; see, e.g., GenBank Accession No. M26596), Calnexin (see, e.g., Wada et al. (1991) *J. Biol. Chem.* 266:19599-19610; GenBank Accession No. M94859), and Calreticulin (see, e.g., Michalak et al. (1992) *Biochem J* 285 (Pt 3):681-92; Fliegel et al. (1989) *J Biol Chem* 264(36): 21522-8; GenBank Accession No. NM_004343), can be used. In addition, reticulocalbin, an ER-resident calcium-binding protein can be used (see, e.g., Ozawa et al. (1993) *J. Biol. Chem.* 268:699-705). It will be appreciated that any variant, derivative, fragment, or allele of any of these genes or gene products can be used.

As discussed supra, without being bound by the following theory, it is speculated that the herein described effects of ER resident chaperones on the generation of active thrombin on the surface of cells is mediated by calcium, i.e., the chaperones sequester free calcium within the secretory pathway, thereby preventing the generation of active TF on the surface of the cells and, in turn, preventing the generation of active thrombin. Accordingly, any treatment, compound, protein, or polynucleotide can be used that decreases the level of free calcium in the secretory pathway, e.g., GRP78/BiP, reticulocalbin, Calreticulin, or Calnexin.

Further, any treatment, factor, or condition that increases the level or activity of an ER resident chaperone protein can be used, including those that adversely affect protein processing and folding in the ER (e.g., homocysteine and other sulfhydryl-reducing agents, unassembled protein subunits within the ER, overexpression and aggregation of proteins within the ER), treatments known to affect cellular glycosylation (e.g., glucose starvation, tunicamycin, 2-deoxyglucose, glucosamine), treatments known to affect intracellular $Ca^{2+}$ levels (e.g., calcium ionophores A23187 and ionomycin, calcium chelating agents, EGTA, calcium ATPase inhibitors, thapsigargin), or other treatments and/or conditions including ethanol, hypoxia, insulin, tissue injury, and low extracellular pH.

In certain embodiments, a growth factor will be administered to the cell that induces the expression of ER chaperone proteins. For example, IL-3 and other cytokines have been shown to induce the expression of ER chaperones such as GRP78/BiP and GRP94. See, e.g., Brewer et al., (1997) *EMBO J.* 16:7207-7216. Significantly, this effect of IL-3 occurs without inducing the unfolded protein response (UPR) pathway, as evidenced by the absence of expression of the transcription factor CHOP.

The expression of any of the herein-described genes can be induced using any of a number of methods, including, but not limited to, introducing nucleic acids encoding the gene product into cells, introducing nucleic acids encoding a protein that induces the expression or activation of the protein of interest, or by administering to a mammal a compound that induces the expression of the gene.

1. Introducing Nucleic Acids Into Cells

In numerous embodiments, one or more nucleic acids, e.g., a GRP78/BiP-encoding polynucleotide, is introduced into cells in vitro or in vivo. Accordingly, the present invention provides methods, reagents, vectors, and cells useful for the expression of GRP78/BiP and other ER resident chaperone proteins and nucleic acids using in vitro (cell-free), ex vivo or in vivo (cell or organism-based) recombinant expression systems. Such methods are useful for a number of applications, for example to treat or prevent a thromboembolic condition or disease in a patient, to modulate the level of TF activity and/or thrombin activity on the surface of a cell, e.g., to investigate the role of TF or thrombin in coagulation, or to create cells useful in the screening of test agents for the ability to modulate ER resident chaperone expression or activity.

For use in the present invention, any standard procedure for introducing foreign nucleotide sequences into host cells may be used including, but not limited to, calcium phosphate transfection, spheroplasts, electroporation, liposomes, microinjection, plasma vectors, viral vectors, and any other method for introducing cloned genomic DNA, cDNA, synthetic DNA or other foreign genetic material into a host cell (see, e.g., Berger and Kimmel, *Guide to Molecular Cloning Techniques, Methods in Enzymology* volume 152 Academic Press, Inc., San Diego, Calif. (Berger), F. M. Ausubel et al., eds., Current Protocols, a joint venture between Greene Publishing Associates, Inc. and John Wiley & Sons, Inc., (supplemented through 1999), and Sambrook et al., *Molecular Cloning—A Laboratory Manual* (2nd Ed.), Vol. 1-3, Cold Spring Harbor Laboratory, Cold Spring Harbor, N.Y., 1989.

Preparation of various polynucleotides and vectors useful in the present invention are well known. General texts which describe methods of making recombinant nucleic acids include Sambrook et al., supra; Ausubel et al., supra; and Berger and Kimmel, *Guide to Molecular Cloning Tech-* niques, *Methods in Enzymology*, volume 152 Academic Press, Inc., San Diego, Calif. (Berger). In numerous embodiments of this invention, nucleic acids will be inserted into vectors using standard molecular biological techniques. Vectors may be used at multiple stages of the practice of the invention, including for subcloning nucleic acids encoding, e.g., components of proteins or additional elements controlling protein expression, vector selectability, etc. Vectors may also be used to maintain or amplify the nucleic acids, for example by inserting the vector into prokaryotic or eukaryotic cells and growing the cells in culture.

Product information from manufacturers of biological reagents and experimental equipment also provide information useful in known biological methods such as cloning. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., Applied Biosystems (Foster City, Calif.), Digene Diagnostics, Inc. (Beltsville, Md.) as well as many other commercial sources known to one of skill. These commercial suppliers produce extensive catalogues of compounds, products, kits, techniques and the like for performing a variety of standard methods.

A convenient method of introducing the polynucleotides into cells in vivo and in vitro involves the use of viral vectors, e.g., adenoviral vector mediated gene delivery (see, e.g., Chen et al. (1994) *Proc. Nat'l. Acad. Sci. USA* 91:3054-3057; Tong et al. (1996) *Gynecol. Oncol.* 61:175-179; Clayman et al. (1995) *Cancer Res.* 5:1-6; O'Malley et al. (1995) *Cancer Res.* 55:1080-1085; Hwang et al. (1995) *Am. J. Respir. Cell Mol. Biol.* 13:7-16; Haddada et al. (1995) *Curr. Top. Microbiol. Immunol.* 199 (Pt. 3):297-306; Addison et al. (1995) *Proc. Nat'l. Acad. Sci. USA* 92:8522-8526; Colak et al. (1995) *Brain Res.* 691:76-82; Crystal (1995) *Science* 270:404-410; Elshami et al. (1996) *Human Gene Ther.* 7:141-148; Vincent et al. (1996) *J. Neurosurg.* 85:648-654); and retroviral vectors (see, e.g., Marx et al. *Hum Gene Ther* 1999 May 1;10(7): 1163-73; Mason et al. (1998) *Gene Ther.* 5(8):1098-104). In addition, replication-defective retroviral vectors harboring a therapeutic polynucleotide sequence as part of the retroviral genome have also been used, particularly with regard to simple MuLV vectors. See, e.g., Miller et al. (1990) *Mol. Cell. Biol.* 10:4239; Kolberg (1992) *J. NIH Res.* 4:43, and Cornetta et al. *Hum.* (1991) *Gene Ther.* 2:215. Other suitable retroviral vectors include lentiviruses (Klimatcheva et al., (1999) *Front Biosci* 4:D481-96). Other viral vectors that can be used in the present invention include vectors derived from adeno-associated viruses (Bueler (1999) *Biol Chem* 380(6):613-22; Robbins and Ghivizzani (1998) *Pharmacol. Ther.* 80(1):35-47), herpes simplex viruses (Krisky et al. (1998) *Gene Ther.* 5(11): 1517-30), and others.

Plasmid vectors can also be delivered as "naked" DNA or combined with various transfection-facilitating agents. Numerous studies have demonstrated the direct administration of naked DNA, e.g., plasmid DNA, to cells in vivo (see, e.g., Wolff (1997) *Neuromuscul. Disord.* 7(5):314-8, Nomura et al. (1999) *Gene Ther.* 6(1):121-9). For certain applications it is possible to coat the DNA onto small particles and project genes into cells using a device known as a gene gun.

Plasmid DNA can also be combined with any of a number of transfection-facilitating agents. The most commonly used transfection facilitating agents for plasmid DNA in vivo have been charged and/or neutral lipids (Debs and Zhu (1993) WO 93/24640 and U.S. Pat. No. 5,641,662; Debs U.S. Pat. No. 5,756,353; Debs and Zhu Published EP Appl. No. 93903386; Mannino and Gould-Fogerite (1988) *BioTechniques* 6(7):682-691; Rose U.S. Pat. No. 5,279,833; Brigham (1991) WO 91/06309 and U.S. Pat. No. 5,676,954; and Felgner et al. (1987) *Proc. Natl. Acad. Sci. USA* 84:7413-7414). Additional useful liposome-mediated DNA transfer methods, other than the references noted above, are described in U.S. Pat. Nos. 5,049,386; 4,946,787; and 4,897,355; PCT publications WO 91/17424, WO 91/16024; Wang and Huang (1987) *Biochem. Biophys. Res. Commun.* 147:980; Wang and Huang (1989) *Biochemistry* 28:9508; Litzinger and Huang (1992) *Biochem. Biophys. Acta* 1113:201; Gao and Huang (1991) *Biochem. Biophys. Res. Commun.* 179:280. Immunoliposomes have been described as carriers of exogenous polynucleotides (Wang and Huang (1987) *Proc. Natl. Acad. Sci. U.S.A.* 84:7851; Trubetskoy et al. (1992) *Biochem. Biophys. Acta* 1131:311) and may have improved cell type specificity as compared to liposomes by virtue of the inclusion of specific antibodies which presumably bind to surface antigens on specific cell types. Behr et al. (1989) *Proc. Natl. Acad. Sci. U.S.A.* 86:6982 report using lipopolyamine as a reagent to mediate transfection itself, without the necessity of any additional phospholipid to form liposomes.

Lipid carriers usually contain a cationic lipid and a neutral lipid. Most in vivo transfection protocols involve forming liposomes made up of a mixture of cationic and neutral lipid and complexing the mixture with a nucleic acid. The neutral lipid is often helpful in maintaining a stable lipid bilayer in liposomes used to make the nucleic acid:lipid complexes, and can significantly affect transfection efficiency. Liposomes may have a single lipid bilayer (unilamellar) or more than one bilayer (multilamellar). They are generally categorized according to size, where those having diameters up to about 50 to 80 nm are termed "small" and those greater than about 80 to 1000 nm, or larger, are termed "large." Thus, liposomes are typically referred to as large unilamellar vesicles (LUVs), multilamellar vesicles (MLVs) or small unilamellar vesicles (SUVs).

Cationic liposomes are typically mixed with polyanionic compounds (including nucleic acids) for delivery to cells. Complexes form by charge interactions between the cationic lipid components and the negative charges of the polyanionic compounds.

A wide variety of liposomal formulations are known and commercially available and can be tested in the assays of the present invention for precipitation, DNA protection, pH effects and the like. Because liposomal formulations are widely available, no attempt will be made here to describe the synthesis of liposomes in general. Two references which describe a number of therapeutic formulations and methods are WO 96/40962 and WO 96/40963.

Cationic lipid-nucleic acid transfection complexes can be prepared in various formulations depending on the target cells to be transfected. While a range of lipid-nucleic acid complex formulations will be effective in cell transfection, optimal conditions are determined empirically in the desired system. Lipid carrier compositions are evaluated, e.g., by their ability to deliver a reporter gene (e.g., CAT, which encodes chloramphenicol acetyltransferase, luciferase, β-galactosidase, or GFP) in vitro, or in vivo to a given tissue type in an animal, or in assays which test stability, protection of nucleic acids, and the like.

The lipid mixtures are complexed with nucleic acids in different ratios depending on the target cell type, generally ranging from about 6:1 to 1:20 µg nucleic acid:nmole cationic lipid.

For mammalian host cells, viral-based and nonviral, e.g., plasmid-based, expression systems are provided. Nonviral vectors and systems include plasmids and episomal vectors, typically with an expression cassette for expressing a protein or RNA, and human artificial chromosomes (see, e.g., Harrington et al. (1997) Nat. Genet. 15:345). For example, plasmids useful for expression of polynucleotides and polypeptides in mammalian (e.g., human) cells include pcDNA3.1/His, pEBVHis A, B & C, (Invitrogen, San Diego Calif.), MPSV vectors, others described in the Invitrogen 1997 Catalog (Invitrogen Inc, San Diego Calif.), which is incorporated in its entirety herein, and numerous others known in the art for other proteins.

Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). SFV and vaccinia vectors are discussed generally in Ausubel et al., supra, Ch. 16. These vectors are often made up of two components, a modified viral genome and a coat structure surrounding it (see generally, Smith (1995) Ann. Rev. Microbiol. 49:807), although sometimes viral vectors are introduced in naked form or coated with proteins other than viral proteins. However, the viral nucleic acid in a vector may be changed in many ways, for example, when designed for gene therapy. The goals of these changes are to disable growth of the virus in target cells while maintaining its ability to grow in vector form in available packaging or helper cells, to provide space within the viral genome for insertion of exogenous DNA sequences, and to incorporate new sequences that encode and enable appropriate expression of the gene of interest.

Thus, viral vector nucleic acids generally comprise two components: essential cis-acting viral sequences for replication and packaging in a helper line and the transcription unit for the exogenous gene. Other viral functions are expressed in trans in a specific packaging or helper cell line. Adenoviral vectors (e.g., for use in human gene therapy) are described in, e.g., Rosenfeld et al. (1992) Cell 68:143; PCT publications WO 94/12650; 94/12649; and 94/12629. In cases where an adenovirus is used as an expression vector, a sequence may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc. Natl. Acad. Sci. USA 81:3655). Replication-defective retroviral vectors harboring a therapeutic polynucleotide sequence as part of the retroviral genome are described in, e.g., Miller et al. (1990) Mol. Cell. Biol. 10:4239; Kolberg (1992) J. NIH Res. 4:43; and Cornetta et al. (1991) Hum. Gene Ther. 2:215. In certain embodiments, the surface of the virus can be coated, e.g., by covalent attachment, with polyethylene glycol (PEG; see, e.g., O'Riordan et al. (1999) Hum. Gene Ther. 10(8): 1349-58.). Such "PEGylation" of viruses can impart various benefits, including increasing the infectivity of the virus, and lowering the host immune response to the virus.

A variety of commercially or commonly available vectors and vector nucleic acids can be converted into a vector of the invention by cloning a polynucleotide of this invention into the commercially or commonly available vector. A variety of common vectors suitable for this purpose are well known in the art. For cloning in bacteria, common vectors include pBR322 derived vectors such as pBLUESCRIPT™, and bacteriophage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Typically, a nucleic acid subsequence encoding a polypeptide, e.g., an ER resident chaperone protein, is placed under the control of a promoter. A nucleic acid is "operably linked" to a promoter when it is placed into a functional relationship with the promoter. For instance, a promoter or enhancer is operably linked to a coding sequence if it increases or otherwise regulates the transcription of the coding sequence. Similarly, a "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include promoters and, optionally, introns, polyadenylation signals, and transcription termination signals. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An extremely wide variety of promoters are well known, and can be used in the vectors of the invention, depending on the particular application. Ordinarily, the promoter selected depends upon the cell in which the promoter is to be active. In mammalian cell systems, promoters from mammalian genes or from mammalian viruses are often appropriate. Suitable promoters may be constitutive, cell type-specific, stage-specific, and/or inducible or repressible (e.g., by hormones such as glucocorticoids). Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art. In one embodiment, the promoter normally associated with the polynucleotide is used, e.g., to express GRP78/BiP, a GRP78/BiP promoter is used (see, e.g., GenBank Accession No. X59969).

Other expression control sequences such as ribosome binding sites, transcription termination sites and the like are also optionally included. For E. coli, example control sequences include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, a retrovirus (e.g., an LTR based promoter) etc., and a polyadenylation sequence, and may include splice donor and acceptor sequences.

2. Inducing ER Resident Chaperones Using Heterologous Compounds

In numerous embodiments of this invention, the level of active thrombin generation on the surface of a cell will be induced by administering to the cell, in vivo or in vitro, any of a large number of potential ER resident chaperone-inducing molecules, e.g., polypeptides, antibodies, amino acids, nucleotides, lipids, carbohydrates, or any organic or inorganic molecule. Such modulators are particularly useful in the prevention or treatment of any of a large number of thromboembolic diseases or conditions.

In one embodiment, a growth factor, e.g., a cytokine such as IL-3 is used to induce the expression of a chaperone such as GRP78/BiP (see, e.g., Brewer et al., supra).

To identify molecules capable of modulating ER resident chaperones, assays will be performed to detect the effect of various compounds on the level or activity of the chaperone. Such assays can involve the identification of compounds that interact with the chaperone proteins, either physically or genetically, and can thus rely on any of a number of standard methods to detect physical or genetic interactions between compounds. Such assays can also involve the identification of compounds that affect ER resident chaperone expression, activity or other properties, such as its phosphorylation state or ability to bind other proteins. Such assays can also involve the detection of ER resident chaperone activity in a cell, either in vitro or in vivo. Such cell-based assays can be performed in any type of cell, e.g., a cell that naturally expresses an ER resident chaperone, or a cultured cell that produces the chaperone due to recombinant expression.

In a preferred embodiment, the cells used in such assays are bladder carcinoma cell lines such as T24/83 cells (see, Examples section).

In numerous embodiments, a compound will be identified that induces the expression of an ER resident chaperone protein such as GRP78/BiP, e.g., by increasing its transcription, translation, mRNA stability, etc. For example, to identify agents that induce the expression of, e.g., GRP78/BiP, a preferred "screening" method involves (i) contacting a cell capable of expressing GRP78/BiP with a test agent; and (ii) detecting the level of GRP78/BiP expression in the presence and absence of the test agent, where an increased level of expression in the presence of the test agent in comparison to the level of expression in the absence of the test agent indicates that the test agent increases or induces the expression of the protein.

Such modulators of expression or activity of an ER resident chaperone proteins can also involve detecting the ability of a test agent to bind to or otherwise interact with the protein, or with a nucleic acid sequence, e.g., a promoter, encoding or regulating the expression of the protein.

In any of the herein described embodiments, a compound that causes an increase in the level or activity of the ER resident chaperone protein can be used to decrease the accumulation of active thrombin or TF PCA on the surface of cells. In contrast, compounds that cause a decrease in the level or activity of the ER resident chaperone protein can be used to increase the accumulation of active thrombin or TF PCA on the surface of cells.

In preferred embodiments, compounds found to increase the expression or activity of an ER resident chaperone will not cause an associated increase in ER stress (i.e., the induction of the chaperone is preferably direct and not occurring in response to an induction of ER stress). The effect of a candidate ER resident chaperone inducer on ER stress can be detected, using any of a number of methods, including by detecting the expression or activation of any ER stress-responsive gene or gene product, including, but not limited to, GRP78/BiP, NFκB, GADD153, GADD45, Id-1, ATF-4, YY1, cyclin D1, FRA-2, glutathione peroxidase, NKEF-B PAG, superoxide dismutase, and clusterin (Outinen et al. (1999) *Blood* 94:959-967; Outinen et al. (1998) *Biochem. J.* 332:213-221). In addition, ER stress-inducing ability can be detected using a "cell-killing" type assay, where the ability of an agent to kill a cell by ER stress can be determined by comparing the ability of the agent to kill cells in normal cells or in cells expressing an ER protecting factor, such as GRP78/BiP. Agents that kill cells only in the absence of such protective factors are identified as ER stress-inducing factors. See, e.g., Morris et al. (1997) *J. Biol. Chem.* 272:4327-34). Agents that affect the level of misfolded proteins can also be used, e.g., to detect modulation of ER stress, by, e.g., detecting misfolded proteins by virtue of their ability to bind to GRP78/BiP.

a) Detection of Polynucleotides

In numerous embodiments, the ability of a test agent to induce an ER resident chaperone protein is monitored by detecting the level of mRNA encoding the ER resident chaperone itself, or of mRNA encoding a protein whose expression is regulated by the ER resident chaperone (e.g., TF, TM, or thrombin). Methods of detecting and/or quantifying the level of a gene transcript using nucleic acid hybridization techniques are known to those of skill in the art (see, Sambrook et al (1989) *Molecular Cloning: A Laboratory Manual*, 2d Ed., vols 1-3, Cold Spring Harbor Press, New York).

For example, one method for evaluating the presence, absence, or quantity of an ER resident chaperone associated cDNA involves a Southern Blot. Briefly, the mRNA is isolated using standard methods and reverse transcribed to produce cDNA. The cDNA is then optionally digested, run on a gel, and transferred to a membrane. Hybridization is then carried out using nucleic acid probes specific for the cDNA and detected using standard techniques (see, e.g., Sambrook et al., supra).

Similarly, a Northern blot may be used to detect an mRNA directly. In brief, in a typical embodiment, mRNA is isolated from a population of cells, electrophoresed to separate the mRNA species, and transferred from the gel to a nitrocellulose membrane. As with the Southern blots, labeled probes are then hybridized to the membrane to identify and/or quantify the mRNA.

In another preferred embodiment, a transcript (e.g., mRNA) is detected using amplification-based methods (e.g., RT-PCR). RT-PCR methods are well known to those of skill (see, e.g., Ausubel et al, supra). Preferably, quantitative RT-PCR is used, thereby allowing the comparison of the level of mRNA in a sample with a control sample or value.

b) Detection of Polypeptides

In other embodiments, the functional effect of a test agent is monitored by detecting the level of an ER resident chaperone protein or of a protein that is regulated by an ER resident chaperone protein, e.g., thrombin, TF, or TM. The level of any polypeptide, e.g., an ER resident chaperone protein, thrombin, TF, or TM, can be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In a preferred embodiment, one of the above-recited polypeptides is detected using an immunoassay such as an ELISA assay (see, e.g., Crowther, John R. *ELISA Theory and Practice*. Humana Press: New Jersey, 1995). As used herein, an "immunoassay" is an assay that utilizes an antibody to specifically bind to the analyte (i.e., the polypeptide). The immunoassay is thus characterized by detection of specific binding of a polypeptide to an antibody specific to the polypeptide.

In an immunoassay, a polypeptide can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition, *Enzyme Immunoassay* (Maggio, ed., 1980); and Harlow & Lane, supra.

Immunoassays typically rely on direct or indirect labeling methods to detect antibody-analyte binding. For example, an anti-GRP78/BiP antibody can be directly labeled, thereby allowing detection. Alternatively, the anti-GRP78/BiP antibody may itself be unlabeled, but may, in turn, be bound by a labeled third antibody specific to antibodies of the species from which the second antibody is derived. The second or third antibodies can also be modified with a detectable moiety, e.g., as biotin, to which a third labeled molecule can specifically bind, such as enzyme-labeled streptavidin. Also, other antibody-binding molecules can be used, e.g., labeled protein A or G (see, generally Kronval, et al. (1973) *J. Immunol.* 111:1401-1406, and Akerstrom (1985) *J. Immunol.* 135: 2589-2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Immunoassays for detecting a polypeptide can be competitive or noncompetitive. Noncompetitive immunoassays are assays in which the amount of captured analyte is directly measured. In a preferred embodiment, "sandwich" assays will be used, for example, wherein antibodies specific for the analyte are bound directly to a solid substrate where they are immobilized. These immobilized antibodies then capture the protein of interest present in a test sample. The protein thus immobilized is then bound by a labeling agent, such as a second specific antibody bearing a label.

In competitive assays, the amount of protein present in a sample is measured indirectly, e.g., by measuring the amount of added (exogenous) protein displaced (or competed away) from a specific antibody by protein present in a sample. For example, a known amount of labeled GRP78/BiP polypeptide is added to a sample and the sample is then contacted with an anti-GRP78/BiP antibody. The amount of labeled GRP78/BiP polypeptide bound to the antibody is inversely proportional to the concentration of GRP78/BiP polypeptide present in the sample.

Any of a number of labels can be used in any of the immunoassays of this invention, including fluorescent labels, radioisotope labels, or enzyme-based labels, wherein a detectable product of enzyme activity is detected (e.g., peroxidase, alkaline phosphatase, β-galactosidase, etc.).

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such nonspecific binding are well known to those of skill in the art. Typically, this technique involves coating the substrate with a proteinaceous composition. In particular, protein compositions such as bovine serum albumin (BSA), nonfat powdered milk, and gelatin are widely used.

Methods of producing polyclonal and monoclonal antibodies that react specifically with a protein are known to those of skill in the art (see, e.g., Coligan (1991) *Current Protocols in Immunology;* Harlow & Lane, supra; Goding, *Monoclonal Antibodies: Principles and Practice* (2d ed. 1986); and Kohler & Milstein (1975) *Nature* 256:495-497. Such techniques include antibody preparation by selection of antibodies from libraries of recombinant antibodies in phage or similar vectors, as well as preparation of polyclonal and monoclonal antibodies by immunizing rabbits or mice (see, e.g., Huse et al. (1989) *Science* 246:1275-1281; Ward et al. (1989) *Nature* 341:544-546).

A number of peptides or a full length protein may be used to produce antibodies specifically reactive with a protein of interest. For example, recombinant protein can be expressed in eukaryotic or prokaryotic cells and purified using standard methods. Recombinant protein is the preferred immunogen for the production of monoclonal or polyclonal antibodies. Alternatively, a synthetic peptide derived from any amino acid sequence can be conjugated to a carrier protein and used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the protein. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein (1976) *Eur. J. Immunol.* 6:511-519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science* 246:1275-1281.

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-specific proteins or even other related proteins from other organisms, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

c) Detection of ER Resident Chaperone-Binding Compounds

In certain embodiments, assays will be performed to identify molecules that physically or genetically interact with ER resident chaperone proteins. Such molecules can be any type of molecule, including polypeptides, polynucleotides, amino acids, nucleotides, carbohydrates, lipids, or any other organic or inorganic molecule. Such molecules may represent molecules that normally interact with ER resident chaperones, or may be synthetic or other molecules that are capable of interacting with ER resident chaperones and that can potentially be used to modulate ER resident chaperone activity in cells, or used as lead compounds to identify classes of molecules that can interact with and/or modulate ER resident chaperones. Such assays may represent physical binding assays, such as affinity chromatography, immunoprecipitation, two-hybrid screens, or other binding assays, or may represent genetic assays as described infra.

In any of the binding or functional assays described herein, in vivo or in vitro, any ER resident chaperone protein, or any derivative, variant, homolog, or fragment of an ER resident chaperone protein, can be used. In numerous embodiments, a fragment of an ER resident chaperone protein is used.

Compounds that interact with ER resident chaperone proteins can be isolated based on an ability to specifically bind to an ER resident chaperone protein or fragment thereof. In numerous embodiments, the ER resident chaperone protein or protein fragment is attached to a solid support. In one embodiment, affinity columns are made using the ER resident chaperone polypeptide, and physically-interacting molecules are identified. It will be apparent to one of skill that chromatographic techniques can be performed at any scale and using equipment from many different manufacturers (e.g., Pharmacia Biotech). In addition, molecules that interact with ER resident chaperone proteins in vivo can be identified by co-immunoprecipitation or other methods, i.e., immunoprecipitating ER resident chaperone proteins using anti-ER resident chaperone antibodies, e.g., anti GRP78/BiP antibodies, from a cell or cell extract, and identifying compounds, e.g., proteins, that are precipitated along with the ER resident chaperone protein. Such methods are well known to those of skill in the art and are taught, e.g., in Ausubel et al., Sambrook et al., Harlow & Lane, all supra.

Two-hybrid screens can also be used to identify polypeptides that interact in vivo with an ER resident chaperone polypeptide or a fragment thereof (Fields et al. (1989) *Nature* 340:245-246). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides do in fact interact in vivo, then the DNA binding and the transcriptional activating domain of the transcription factor are united, thereby producing expression of a target gene in the cell. The target gene typically encodes an easily detectable gene product, e.g., β-galactosidase, GFP, or luciferase, which can be detected using standard methods. In the present invention, an ER resident chaperone polypeptide, or fragment thereof, is fused to one of the two domains of the transcription factor, and the potential ER resident chaperone-binding polypeptides (e.g., encoded by a cDNA library) are fused to the other domain. Such methods are well known to those of skill in the art, and are taught, e.g., in Ausubel et al., supra.

d) Assays for ER Resident Chaperone Protein Activity

The effects of a test compound upon the function of an ER resident chaperone protein can also be measured by examining any suitable physiological change that is affected by ER resident chaperone activity. For example, the ability of ER resident chaperones to protect cells from oxidative or ER stress can be detected. When the functional consequences are determined using intact cells or animals, one can also measure a variety of effects that are indicative of decreased thrombin levels, e.g., inhibition of atherosclerosis or other cardiovascular conditions, prevention of thrombosis, etc.

3. Test Agents

Virtually any agent can be tested in the presently described assays, including, but not limited to, natural or synthetic nucleic acids, natural or synthetic polypeptides, natural or synthetic lipids, natural or synthetic small organic molecules, and the like. In one preferred format, test agents are provided as members of a combinatorial library. In preferred embodiments, a collection of small molecules are tested for the ability to modulate the expression or activity of an ER resident chaperone gene or gene product. A "small molecule" refers to any molecule, e.g., a carbohydrate, nucleotide, amino acid, oligonucleotide, oligopeptide, lipid, inorganic compound, etc. that can be tested in such an assay. Such molecules can modulate the expression or activity of any of the herein-recited genes or gene products by any of a number of mechanisms, e.g., by binding to a promoter and modulating the expression of the encoded protein, by binding to an mRNA and affecting its stability or translation, or by binding to a protein and competitively or non-competitively affecting its interaction with, e.g., other proteins in the cell. Further, such molecules can affect the protein directly or indirectly, i.e., by affecting the expression or activity of a regulatory of the protein. Preferably, such "small molecule inhibitors" are smaller than about 10 kD, preferably 5, 2, or 1 kD or less.

As discussed above, test agents can be screened based on any of a number of factors, including, but not limited to, a level of a polynucleotide, e.g., mRNA, of interest, a level of a polypeptide, the degree of binding of a compound to a polynucleotide or polypeptide, the intracellular localization of a polynucleotide or polypeptide, any biochemical properties of a polypeptide, e.g., phosphorylation or glycosylation, or any functional properties of a protein, such as the ability of the protein to induce the expression of other genes or to induce cholesterol biosynthesis. Such direct and indirect measures of protein activity in vivo can readily be used to detect and screen for molecules that modulate the activity of the protein.

a) Combinatorial Libraries

In certain embodiments, combinatorial libraries of potential modulators will be screened for an ability to bind to a polypeptide or to modulate the activity of the polypeptide. Conventionally, new chemical entities with useful properties are generated by identifying a chemical compound (called a "lead compound") with some desirable property or activity, e.g., GRP78/BiP activating activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et al. (1994) *J. Med. Chem.* 37(9):1233-1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37:487-493, Houghton et al. (1991) *Nature,* 354:84-88), peptoids (PCT Publication No WO 91/19735, Dec. 26, 1991), encoded peptides (PCT Publication WO 93/20242, Oct. 14. 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al (1993) *Proc. Nat. Acad. Sci. USA* 90:6909-6913), vinylogous polypeptides (Hagihara et al (1992) *J. Amer. Chem. Soc.* 114:6568), nonpeptidal peptidomimetics with a Beta-D-Glucose scaffolding (Hirschmann et al. (1992) *J. Amer. Chem. Soc.* 114:9217-9218), analogous organic syntheses of small compound libraries (Chen et al. (1994) *J. Amer. Chem. Soc.* 116:2661), oligocarbamates (Cho, et al. (1993) *Science* 261: 1303), and/or peptidyl phosphonates (Campbell et al. (1994) *J. Org. Chem.* 59:658). See, generally, Gordon et al. (1994) *J. Med. Chem.* 37:1385, nucleic acid libraries (see, e.g., Strategene Corp.), peptide nucleic acid libraries (see, e.g., U.S. Pat. No. 5,539,083), antibody libraries (see, e.g., Vaughn et al. (1996) *Nature Biotechnology,* 14(3):309-314), and PCT/ US96/10287), carbohydrate libraries (see, e.g., Liang et al. (1996) *Science* 274:1520-1522, and U.S. Pat. No. 5,593,853), and small organic molecule libraries (see, e.g., benzodiazepines, Baum (1993) C&EN, January 18, page 33; isoprenoids, U.S. Pat. No. 5,569,588; thiazolidinones and methathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288, 514; and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well-known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

b) High Throughput Screening

Any of the assays to identify compounds capable of modulating the expression or activity of any of the genes or gene products described herein are easily amenable to high throughput screening.

High throughput assays for the presence, absence, quantification, or other properties of test agents on cells are well known to those of skill in the art. Similarly, binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

III. Administration of ER Resident Chaperone-Modulating Compounds

In numerous embodiments of the present invention, a compound useful in the treatment or prevention of a thromboembolic disorder, i.e., a polynucleotide, polypeptide, test agent, or any compound that increases levels of GRP78/BiP mRNA, polypeptide and/or protein activity, is administered to a mammal. Such compounds can be administered to the mammal to inhibit the generation of thrombin on cells within the mammal, e.g., endothelial cells present at an atherosclerotic plaque within the mammal.

The administration of such compounds can be used to prevent or treat any of a number of thrombotic conditions or diseases. For example, as intravascular coagulation is associated with atherosclerosis, myocardial infarction, and acute arterial thrombosis following plaque disruption, the compounds can be used to prevent or treat any of these conditions or diseases. The compounds can thus be used to prevent thrombin accumulation on the surface of cells in the endothelium of patients who have had a myocardial infarction and who are undergoing angioplasty or stenting, thereby reducing the risk of thrombosis. In addition, the compounds can be administered to patients undergoing cranial radiation to prevent radiation-related thrombotic events. In addition, the compounds can be administered to patients undergoing vascular surgery to prevent surgery related thrombosis. In addition, as TF-induced thrombin generation plays a critical role in hemostasis following tissue injury and also in the pathogenesis of multiple thrombotic disorders associated with a wide range of diseases including, but not limited to, cardiovascular disease, sepsis, and cancer, the present methods can also be used to treat or prevent these diseases and conditions.

Such compounds can be administered by a variety of methods including, but not limited to, parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include, but are not limited to, powder, tablets, pills, capsules and lozenges. It is recognized that the modulators (e.g., antibodies, antisense constructs, ribozymes, small organic molecules, etc.) when administered orally, must be protected from digestion. This is typically accomplished either by complexing the molecule(s) with a composition to render it resistant to acidic and enzymatic hydrolysis, or by packaging the molecule(s) in an appropriately resistant carrier, such as a liposome. Means of protecting agents from digestion are well known in the art.

The compositions for administration will commonly comprise an inducer of an ER resident chaperone dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing inducers of ER resident chaperones can be administered for therapeutic or prophylactic treatments. In therapeutic applications, compositions are administered to a patient suffering from a disease (e.g., atherosclerosis) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of an ER resident chaperone inducer that is capable of preventing or slowing the development of the disease or condition in a mammal is referred to as a "prophylactically effective dose." The particular dose required for a prophylactic treatment will depend upon the medical condition and history of the mammal, the particular disease or condition being prevented, as well as other factors such as age, weight, gender, etc. Such prophylactic treatments may be used, e.g., in a mammal who has previously had the disease or condition to prevent a recurrence of the disease or condition, or in a mammal who is suspected of having a significant likelihood of developing the disease or condition.

It will be appreciated that any of the present ER resident chaperone inducing compounds can be administered alone or in combination with additional ER resident chaperone inducing compounds or with any other therapeutic agent, e.g., other anti-atherosclerotic or other cholesterol-reducing agents or treatments.

IV. Kits

For use in the prophylactic and therapeutic applications suggested above, kits are also provided by the invention. In the diagnostic and research applications such kits may include any or all of the following: assay reagents, buffers, ER resident chaperone nucleic acids or antibodies, hybridization probes and/or primers, small molecule inducers of ER resident chaperone proteins, etc. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to Internet sites that provide such instructional materials.

II. EXAMPLES

A. Stable Overexpression of Human GRP78/BiP in T24/83 Cells

In order to address the role of GRP78/BiP in cell surface thrombin generation and/or inactivation, human GRP78/BiP was stably overexpressed in cells of the human transitional bladder carcinoma cell lines T24/83 (obtained from the American Type Culture Collection; ATCC; Rockville, Md.). T24/83 cells constitutively overexpress active TF on their cell surface and are considered to be procoagulant. Because thrombin generation at the surface of cells is dependent on active TF, these cells were selected as a model system to study the effect of GRP78/BiP overexpression on TF-dependent thrombin generation.

1. Preparation of GRP78/BiP Encoding Vector

To obtain cells stably expressing GRP78/BiP, T24/83 cells were transfected with either the mammalian cell expression vector pcDNA3.1(+) or pcDNA3.1(+) containing the open reading frame of human GRP78/BiP. The latter vector was obtained by amplifying the cDNA encoding the open-reading frame of human GRP78/BiP (approximately 1.95 kb) by reverse transcriptase-PCR using total RNA from primary HUVEC. GRP78/BiP cDNA was generated using SuperScript RNase H reverse transcriptase (Gibco/BRL) and a primer complimentary to a sequence in the 3'-untranslated region of the human GRP78/BiP mRNA transcript (AB10230; 5'-TATTACAGCACTAGCAGATCAGTG-3') (SEQ ID NO:1). For PCR amplification, the forward primer AB10231(5'-CTTAAGCTTGCCACCATGAAGCTCTC-CCTGGTGGCCGCG-3') (SEQ ID NO:2) contained a Kozak consensus sequence (bold) prior to the initiating ATG and a terminal HindIII restriction site (underlined). The reverse primer AB10232 (5'-AGGCCTCGAGCTACAACT-CATCTTTTTCTGCTGT-3') (SEQ ID NO:3) contained a terminal XhoI restriction site (underlined) adjacent to the authentic termination codon of the GRP78/BiP cDNA. PCR reactions took place in a final volume of 50 µl containing 2 µl of the RT reaction, 100 ng of primers, 2.5 U Taq polymerase (Perkin-Elmer, Mississauga, ON) in a buffer consisting of 1.5 mM $MgCl_2$, 50 mM KCl, 10 mM Tris-HCl (pH 8.8) and 0.5 mM of each dNTP. All samples were subjected to amplification in a DNA thermal cycler 480 (Perkin-Elmer) with a step programme of 30 cycles of 94° C. for 1 min 58° C. for 1 min, and 72° C. for 1 min. The amplified GRP78/BiP cDNA was separated on a 0.8% agarose-TBE gel containing ethidium bromide, purified from the agarose gel using the QIAEX gel extraction kit (Qiagen, Mississauga, ON) and ligated into T-ended pBluescript (KS) (Stratagene, La Jolla, Calif.). The ligation mixture was then used to transform competent DH5α cells (Gibco/BRL). Plasmid DNA was isolated from transformed cells using the QIAEX miniprep kit (Qiagen), digested with HindIII and XhoI, and the GRP78/BiP cDNA insert purified from agarose. The GRP78/BiP cDNA insert was ligated into the HindIII/XhoI site of the mammalian expression vector pcDNA3.1(+) (Invitrogen, Carlsbad, Calif.) to produce the recombinant plasmid, pcDNA3.1(+)-GRP78/BiP. Authenticity of the GRP78/BiP cDNA sequence was confirmed by fluorescence-based double stranded DNA sequencing (MOBIX).

2. Isolation of Stably Transfected Cells

T24/83 cells grown to 30% confluency were transfected with 5 µg of the pcDNA3.1I (+)-GRP78/BiP expression plasmid using 30 µl of SuperFect Transfection reagent (Qiagen) as described by the manufacturer. As a vector control, pcDNA3.1l (+) was used to transfect T24/83 under the same conditions. Stable transfectants were selected in complete medium containing 1.2 mg/ml G418 (Gibco/BRL) for two weeks. G418-resistant clones were subsequently identified, isolated and cultured in complete medium containing G418. Overexpression of GRP78/BiP was assessed using immunoblot analysis using an anti-KDEL mAB (SPA-827; StressGen Biotechnologies, Victoria, B. C.) which recognizes both human GRP78/BiP and GRP94. Total protein lysates from T24/83 cells were solubilized in SDS-PAGE sample buffer, heated to 95° for 2 min, separated on SDS-polyacrylamide gels under reducing conditions and transferred to nitrocellulose membranes (Bio-Rad). After incubation with the primary (1 µg/ml) and horseradish peroxidase (HRP)-conjugated secondary antibodies (Gibco/BRL), the membranes were developed using the Renaissance chemiluminescence reagent kit (DuPont/NEN).

Figure 1:
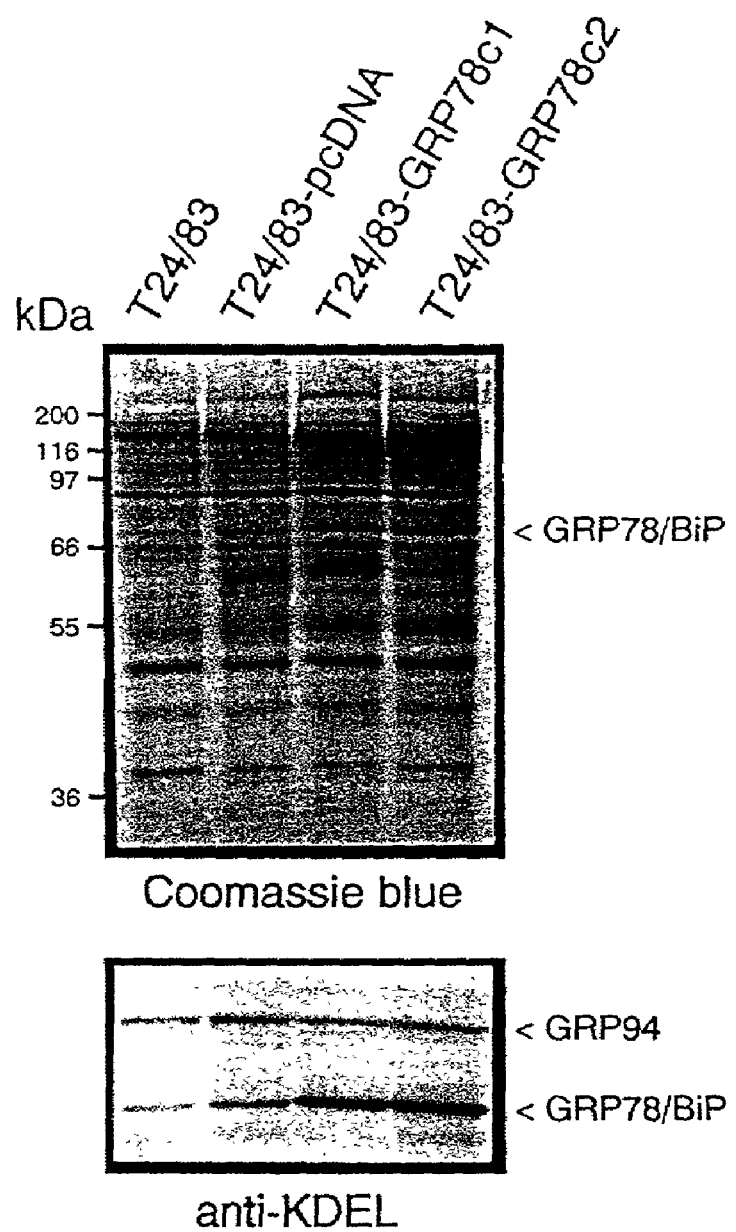
FIG. 1. Stable overexpression of human GRP78/BiP in T24/83 cells. Total protein lysates (30 µg/lane) from wild-type T24/83 cells (T24/83), or cells stably transfected with either the vector pcDNA3.1(+) (T24/83-pcDNA) or pcDNA3.1(+) containing the full-length human GRP78/BiP cDNA (T24/83-GRP78c1 or c2) were separated by SDS-polyacrylamide gel electrophoresis under reducing conditions. Gels were either stained with Coomassie Blue (upper panel) or immunostained with an anti-KDEL mAb which recognizes GRP78/BiP and GRP94 (lower panel). The migration positions of GRP78/BiP and GRP94 are shown by the arrowheads.

As shown in FIG. 1, two independently isolated G418-resistant cell lines, C1 and C2 (designated T24/83-GRP78c1 and c2), respectively), exhibited a 3.3-fold increase in GRP78/BiP protein levels compared to wild-type or vector-transfected cells. In contrast, GRP94 protein levels were unchanged in all cell lines, suggesting that alterations in GRP78/BiP protein levels do not affect endogenous GRP94 protein levels. Unless otherwise stated, the two GRP78/BiP overexpressing T24/83 cell lines C1 and C2, were used interchangeably throughout these studies. Stable cell lines and their vector-transfected counterpart were maintained in a humidified incubator at 37° C. with 5% $CO_2$ in M199 medium (Gibco/BRL) containing 10% fetal bovine serum, 100 µg/ml penicillin and 100 µg/ml streptomycin.

3. Detection of GRP78/BiP Protein Expression in Transfected Cells

To compare the levels and distribution of GRP78/BiP protein, wild type or GRP78/BiP overexpressing cells were cultured on coverslips, fixed, permeabilized and examined in situ by indirect immunofluorescence using anti-GRP78/BiP polyclonal antibodies (Santa Cruz Biotechnology; Santa Cruz, Calif.) (Outinen et al. (1998) *Biochem. J.,* 332:213-221). For detection of cell surface levels of TF, cells were washed with ice-cold 1×PBS for 2 min and incubated with anti-human TF mAb (5 µg/ml) for 1 hr at 4° C. After 3 washes with 1×PBS containing 0.5% FBS, cells were incubated with the appropriate Alexa-labeled secondary antibody (BioLynx, Brockville, Ontario) for 1 hr at 4° C., washed again and fixed with 1% paraformaldehyde. Images were captured and analyzed using Northern Exposure image analysis/archival software (Mississauga, ON)

Figure 2:
FIG. 2. Immunolocalization of GRP78/BiP in T24/83 cells. Wild-type (top panel) or GRP78/BiP overexpressing T24/83 cells (lower panel) plated onto gelatin-coated glass coverslips were fixed, permeabilized and incubated with an anti-KDEL mAb. Antibody localization was detected with a FITC-conjugated goat anti-mouse IgG. Magnification ×1000.
Figure 2:
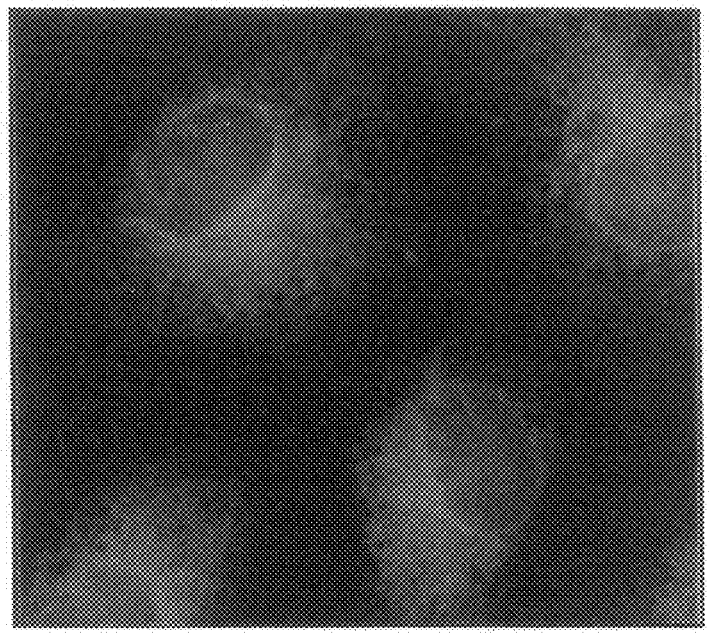

In wild-type cells and GRP78/BiP overexpressing cells, GRP78/BiP was concentrated in the perinuclear region, consistent with its location in the endoplasmic reticulum (FIG. 2). However, the intensity of the immunofluorescent signal was much greater in the GRP78/BiP overexpressing cells, a result consistent with the immunoblot analysis. Non-specific staining was not observed in T24/83 cells immunostained with normal mouse IgG. Overexpression of GRP78/BiP in T24/83 cells suppressed the induction of endogenous GRP78/BiP mRNA levels and increased survival of cell exposed to the ER stress-inducing agent, A23187.

B. Overexpression of GRP78/BiP Decreases Thrombin Generation, Prothrombin Consumption and the Formation of Thrombin-Inhibitor Complexes on T24/83 Cell Surfaces Thrombin generation, prothrombin consumption, and formation of thrombin-inhibitor complexes were determined in normal defibrinated human plasma. Prior to use in the thrombin generation assay, plasmas were defibrinated using arvin, as described previously (Chan et al. (1998) *Lung Cell. Mol. Physiol.* 18:L914-L921). Prothrombin concentrations were determined for each time point during the thrombin generation experiments using a commercially available ELISA kit (Affinity Biologicals). Control plasma with a known concentration of prothrombin was used as a standard.

1. Detecting Thrombin Generation

Total amidolytic activity of thrombin generated on T24/83 cell surfaces was measured as previously described (Ling et al. (1995) *Pediatr. Res.* 37:373-378); Chan et al. (1998) *Lung Cell. Mol. Physiol.* 18:L914-L921). T24183 cell monolayers in 24 well plates were placed on a Thermolyne dri-bath set at 37° C. until the pH of the culture medium had increased to 7.2. After washing twice with 1 ml of acetate-barbital-saline (ABS) buffer, pH 7.4 (0.036 M Na acetate, 0.036 M sodium diethylbarbitarate and 0.145 M NaCl), monolayers were incubated for 3 min with 100 µl of ABS buffer and 200 µl of defibrinated plasma, in the absence or presence of 10% activated partial thromboplastin time (APTT) reagent (Organon Teknika Corp., Durham, N.C.). At various times following the addition of 100 µl of 0.04 M $CaCl_2$ in ABS buffer, 25 µl aliquots of the reaction mixture on the surface of the cells were removed and mixed with 475 µl of 0.005 M $Na_2$ EDTA on ice. Twenty-five µl of each EDTA sample were then mixed with 775 µl of 0.00016 M S-2238 (KabiVitum, Stockholm, Sweden) in buffer and heated to 37° C. for 10 min prior to termination of the amidolytic reaction with 200 µl of 50% acetic acid. The absorbance at 405 nm was measured and the concentration of total thrombin determined by comparing results to a standard curve generated with purified thrombin in S-2238.

EDTA samples were also used to measure the concentrations of prothrombin, thrombin-antithrombin (TAT) complexes and thrombin-heparin cofactor II complexes. Prothrombin, TAT and thrombin-heparin cofactor II complexes were assayed using commercially available ELISA kits (Affinity Biologicals, Hamilton, ON). Because thrombin bound to α2macroglobulin (α2M) retains amidolytic activity against S-2238, the contribution of thrombin-α2M to total thrombin activity was measured. Briefly, the amidolytic activity of total thrombin was measured as described above, except that the 25 µl reaction mixture taken at each time point was incubated with 3.5 µl of 0.15 M NaCl containing 0.25 U standard heparin and 0.042 U antithrombin (to inhibit any free thrombin) for 1 min on ice, followed by the addition of 475 µl $Na_2$ EDTA. Thrombin activity due to α2M-bound thrombin was then subtracted from the total thrombin activity to give the amount of free thrombin generated by the cell surface.

Figure 3:
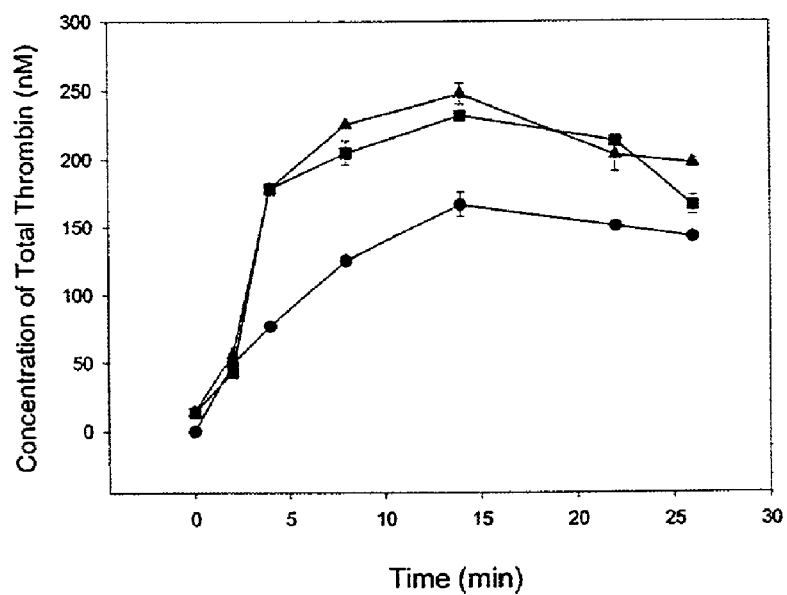
FIG. 3. Overexpression of GRP78/BiP suppresses total (A) and free (B) thrombin generation on T24/83 cell surfaces. Normal pooled human plasma was used to measure total and free thrombin generated on the surface of T24/83 cells. Wild type (▲), vector transfected (■), or GRP78/BiP overexpressing cells (●). Data represent mean ∀ SEM (standard error of the mean, i.e., the standard deviation divided by the square root of sample size) of triplicate measurements from four separate experiments. GRP78/BiP overexpressing cells generated significantly less thrombin compared with wild-type or vector-transfected cells ($p<0.001$).
Figure 3:
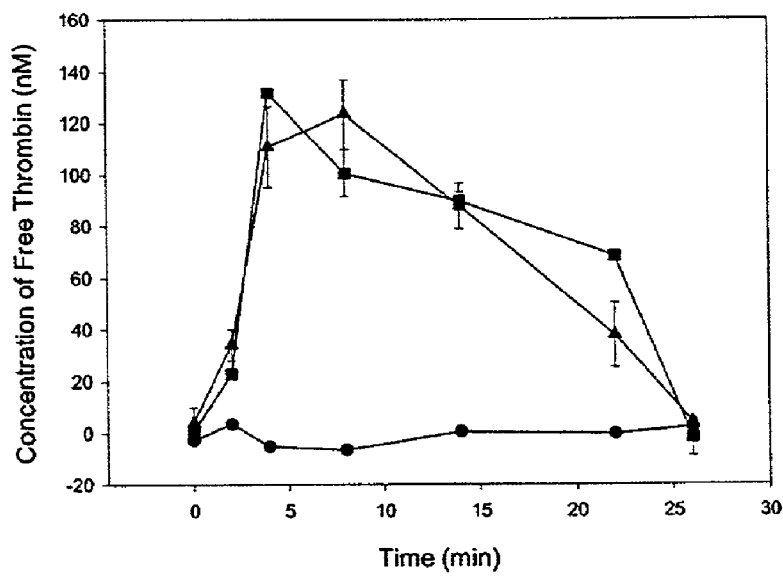

In control plasma, after the addition of calcium, the concentration of total thrombin generated on the cell surface of T24/83 cells overexpressing GRP78/BiP was significantly less after 2 min, relative to wild-type or vector-transfected cells ($p<0.001$) (FIG. 3A). The concentration of free thrombin generated on the surface of T24/83 cells overexpressing GRP78/BiP was negligible for all time points examined, up to 25 min (FIG. 3B). In contrast to the GRP78/BiP overexpressing cells, free thrombin levels generated on the surface of wild-type or vector-transfected T24/83 cells were significantly higher between 2 and 22 min with concentrations reaching 110±16 and 131±2 nM, respectively, by 4 min after the addition of calcium ($p<0.001$).

Figure 4:
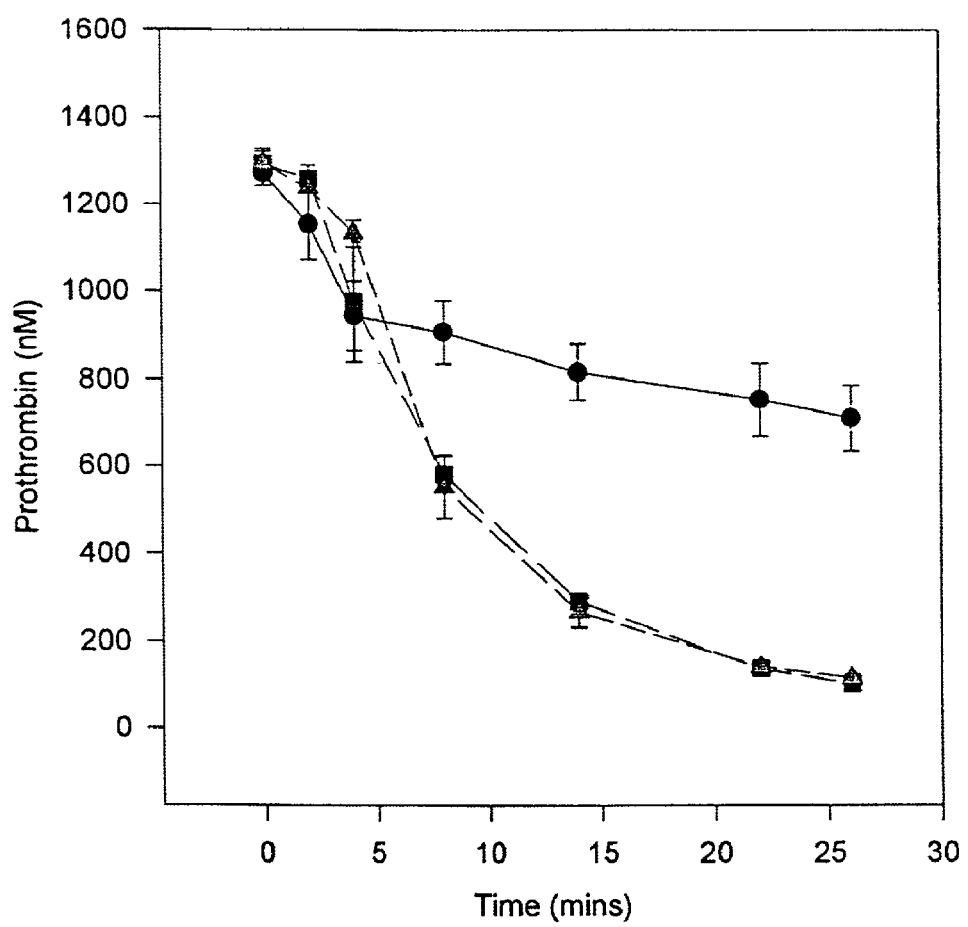
FIG. 4. Overexpression of GRP78/BiP decreases prothrombin consumption on T24/83 cell surfaces. Normal pooled human plasma was used to measure prothrombin consumption on the surface of T24/83 cells. Wild type (▲), vector transfected (■), or GRP78/BiP overexpressing cells (●). Data represent mean ∀ SEM of triplicate measurements from four separate experiments. GRP78/BiP overexpressing cells consumed significantly less prothrombin after 4 min, compared with wild-type or vector-transfected cells ($p<0.001$).

Consistent with these findings, both prothrombin consumption (FIG. 4) and thrombin-inhibitor complexes (Table 1) were significantly reduced in the GRP78/BiP overexpressing cells, compared to wild-type or vector-transfected cells. The observation that the initial rates of thrombin generation (FIG. 3A) and prothrombin consumption (FIG. 4) are similar among all cell lines suggest that cellular factors which either promote or inhibit TF activity, subsequent to initiation, are altered in the GRP78/BiP overexpressing cells.

Figure 5:
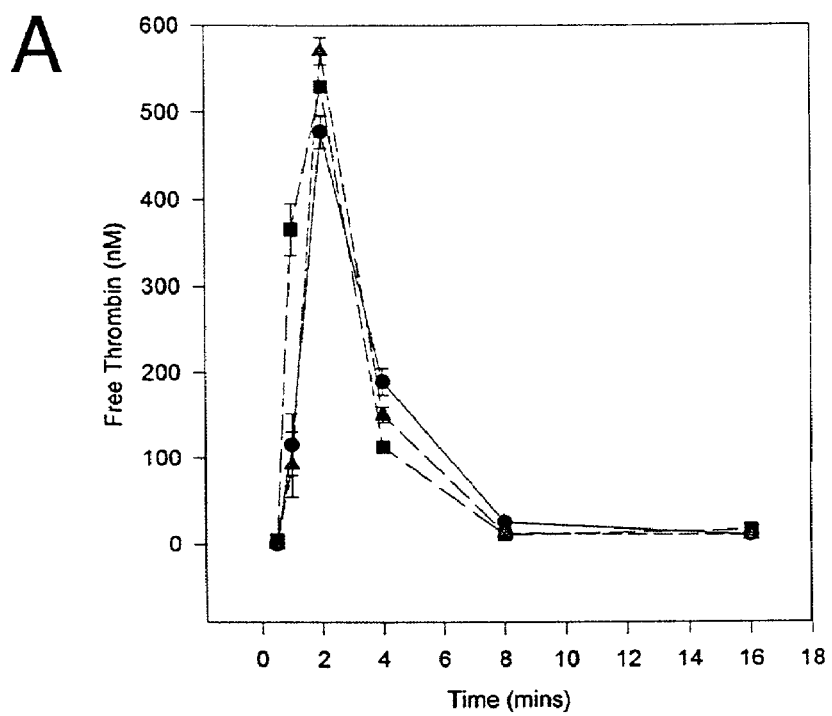
FIG. 5. Effect of GRP78/BiP overexpression on free thrombin generation in normal (A) or factor VII-deficient (B) plasma containing APTT reagent. Normal or factor VII-deficient human plasma, in the presence of APTT reagent, was used to measure free thrombin generation on the surface of T24/83 cells. Wild type (▲), vector transfected (■), or GRP78/BiP overexpressing cells (●). Data representing mean ∀ SEM of triplicate measurements from four separate experiments. In the presence of normal (A), but not factor VII-deficient plasma (B), peak free thrombin generation was significantly decreased in the GRP78/BiP overexpressing cells, compared to wild-type or vector-transfected cells ($p<0.001$).
Figure 5:
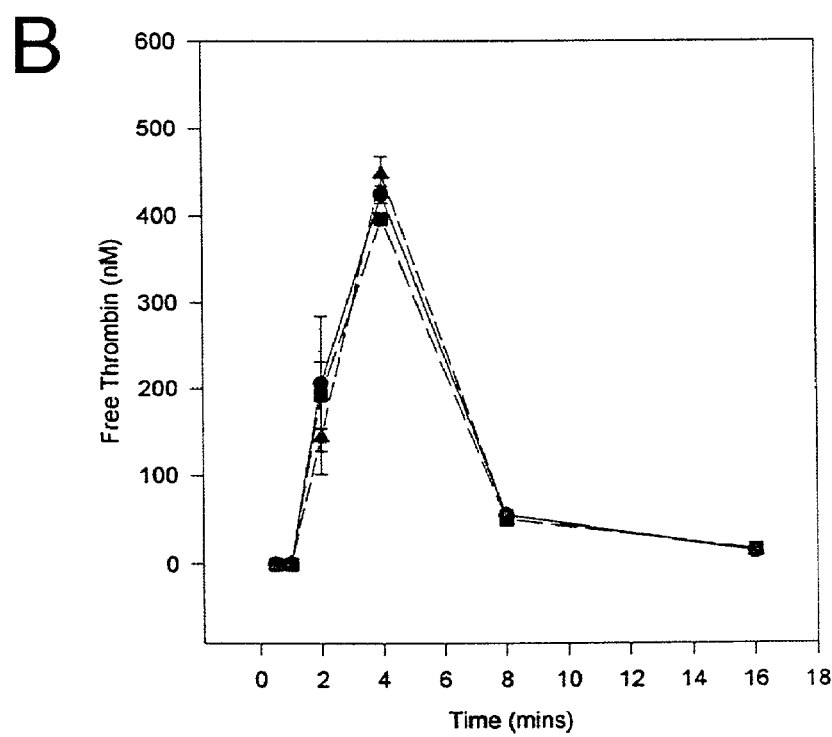

In the presence of APTT reagent, which potentiates thrombin generation through activation of the intrinsic coagulation pathway, concentrations of free thrombin increased among all cell lines examined, with peak levels achieved by 2 min (FIG. 5A). However, peak levels were significantly decreased in T24/83 cells overexpressing GRP78/BiP (480 nM), compared to wild-type (590 nM) and vector-transfected cells (570 nM) ($p<0.05$; n=4).

C. Overexpression of GRP78/BiP Inhibits the Procoagulant Activity (PCA) of Tissue Factor To determine if the effect of GRP78 overexpression on thrombin generation was dependent on the procoagulant activity (PCA) of tissue factor (TF), Factor VII-depleted plasma was used and the results were compared with normal plasma in the absence or presence of APTT reagent. In the absence of APTT reagent, both wild-type and vector-transfected cells had negligible levels of free thrombin generated over the 25 min time period. In the presence of APTT reagent, peak concentrations of free thrombin generated in FVII-depleted plasma was both delayed (4 vs. 2 min) and decreased (FIG. 5B), compared to normal plasma (FIG. 5A). However, there was no significant difference in peak thrombin levels generated in either the wild-type T24/83 cells (460 nM), vector-transfected (410 nM) or GRP78/BiP overexpressing cells (430 nM) in the factor VII-depleted plasma.

The TF-dependent binding and conversion of factor VII to VIIa is the initial step in the extrinsic pathway of blood coagulation. To directly determine whether overexpression of GRP78/BiP decreases TF PCA, the conversion of factor VII to VIIa was measured by a one-step assay using the chromogenic substrate S-2288. Monolayers of wild-type, vector-transfected or GRP78/BiP-overexpressing T24/83 cells were washed in ABS buffer and incubated for time periods up to 30 min in the presence of 108 nM recombinant factor VII and 5 mM $Ca^{2+}$. The amount of factor VIIa generated in the sub-samples of the cell supernatant was assessed by measuring the amidolysis of S-2288 at 405 nm. As shown in Table 2, the conversion of factor VII to VIIa at 30 min on the surface of GRP78/BiP overexpressing cells was decreased approximately 48- and 23-fold compared to wild-type and vector-transfected cells, respectively ($p<0.03$). The observation that the amidolysis of S-2288 did not occur in the absence of factor VII by 30 min (blank control) suggests that amidolysis of the substrate correlates with the generation of factor VIIa and is not due to the presence of other cellular factors known to hydrolyze the substrate (i.e., tissue plasminogen activator, kallikrein). Taken together, these data suggest that the reduction in the procoagulant response on the GRP78/BiP overexpressing cells is mediated by a reduction in TF PCA.

TABLE 1

Thrombin-inhibitor complex formation on T24/83 cell surfaces

| Cell Type | Total inhibitor (nM) | TAT (nM) | IIa-$α_2$M (nM) | IIa-HCII (nM) |
| --- | --- | --- | --- | --- |
| Wild type | 759 ± 18 | 631 ± 13 | 112 ± 5 | 16 ± 0.3 |
| pcDNA | 752 ± 57 | 610 ± 52 | 124 ± 7 | 18 ± 0.4 |
| GRP78/BiP | 266 ± 18[a] | 161 ± 15 | 93 ± 3 | 12 ± 0.6 |

Concentrations of thrombin covalently bound to plasma inhibitors were measured in the EDTA samples collected during the thrombin generation end points. Thrombin-antithrombin (TAT) and thrombin-heparin cofactor II (IIa-HCII) were measured by ELISA, and thrombin-$α_2$ macroglobulin (IIa-$α_2$M) was measured chromogenically after inhibiting free thrombin with antithrombin and heparin. Data are presented as the mean ± SEM of triplicate measurements from four separate experiments.
[a]p = 0.001, compared to wild-type or vector-transfected (pcDNA) controls.

TABLE 2

Tissue factor activity on T24/83 cell surfaces

| Cell Type | $\Delta A_{405}$ ($A_{405}$ sample – $A_{405}$ blank) | [factor VIIa] generated (nM) |
|---|---|---|
| Wild type | 0.026 | 0.01025 |
| pcDNA | 0.024 | 0.00493 |
| GRP78/BiP | 0.017[a] | 0.00021[a] |

Plasma membrane-associated tissue factor (TF) activity was determined as the ability to convert factor VII to factor VIIa. Monolayers were incubated with factor VII in ABS buffer followed by measurement of generated factor VIIa by reaction with a chromogenic substrate (S-2288) and recording the absorbance at 405 nm. Similar reactions were carried out in the absence of factor VII (blank). Results were converted to the concentration of factor VIIa generated (nM) using a standard curve from reactions of S-2288 with known amounts of purified factor VIIa. Data are presented as the average of triplicate measurements from two independent experiments. [a]$p < 0.03$, compared to wild-type or vector-transfected (pcDNA) controls.

D. GRP78/BiP Overexpression Leads to an Increase in TF Expression and Synthesis Northern blot hybridization and immunoblot analysis were used to determine whether the decrease in TF PCA resulted from a decrease in TF expression and/or synthesis. Steady-state TF mRNA levels from wild-type, vector-transfected or GRP78/BiP overexpressing cells were analyzed by Northern blot hybridization using a human TF cDNA probe. Total RNA was isolated from cells using the RNeasy total RNA kit (Qiagen) and separated (10 µg/lane) on 2.2M formaldehyde/1.2% agarose gels. Following transfer on to Zeta-Probe GT nylon membranes (Bio-Rad), the RNA was cross-linked to the membrane using a UV crosslinker (PDI Bioscience, Toronto). cDNA fragments encoding either human GRP78/BiP or TF (1.05 kb NarI/HindIII fragment of human TF cDNA) were labeled with [$\alpha$-$^{32}$P]dCTP (NEN) using a random primed DNA labeling kit (Boehringer Mannheim). After overnight hybridization at 43° C., the membranes were washed as described by the manufacturer, exposed to X-ray film and subjected to autoradiography. Changes in gene expression were quantified using a Storm 860 PhosphorImager and ImageQuant image analysis software (Molecular Dynamics, Sunnyvale, Calif.). As a control for RNA loading, integrated optical densities were normalized to human glyceraldehyde 3-phosphate dehydrogenase (GAPDH).

Figure 6:
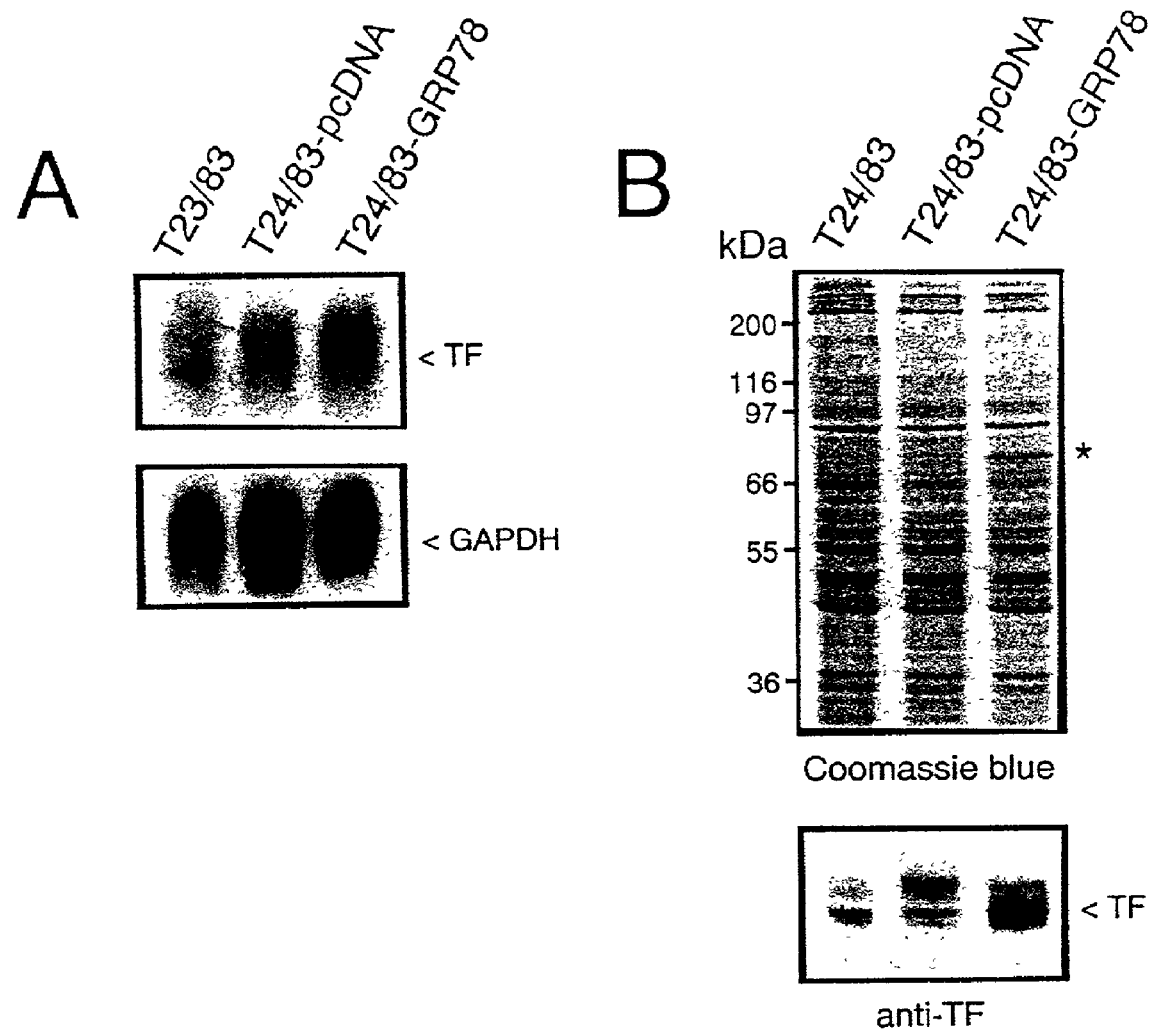
FIG. 6. Overexpression of GRP78/BiP increases TF expression and synthesis. (A) Northern blot hybridization of total RNA (10 µg/lane) from wild type (T24/83), vector transfected (T24/83-pcDNA) or GRP78/BiP overexpressing T24/

In contrast to the decreased TF PCA observed in the GRP78/BiP overexpressing cells, TF mRNA levels were increased approximately 4-fold in these cells, compared to wild-type or vector-transfected cells (FIG. 6A). Consistent with the Northern blot results, immunoblot analysis using anti-human TF mAbs demonstrated that GRP78/BiP overexpressing cells had approximately 2.5-fold greater TF antigen levels, compared to wild-type or vector-transfected cells (FIG. 6B). This increase in total TF antigen levels was confirmed by ELISA. Although total TF protein levels were increased in the GRP78/BiP overexpressing cells, the electrophoretic mobility of TF observed on immunoblots was similar to that of wild-type and vector-transfected cells.

This observation that TF expression, synthesis, and cell surface levels are elevated in GRP78/BiP overexpressing cells suggests that the above-described decrease in thrombin generation does not result from the retention of TF in the ER by GRP78/BiP and that elevated levels of cell surface TF do not compensate for the GRP78/BiP-dependent decrease in TF PCA.

E. Localization of TF on the Cell Surface of T24/83 Cells

To assess whether increased TF antigen levels in the GRP78/BiP overexpressing cells correlated with increased cell surface protein levels, immunofluorescence studies using anti-human TF mAbs were performed on intact wild-type, vector-transfected, or GRP78/BiP overexpressing cells (FIG. 7). All cell types exhibited clusters of TF in defined patches distributed over the cell surface. However, the intensity of TF staining was much greater in the GRP78/BiP overexpressing cells (FIG. 7C) compared to wild type (FIG. 7A) or vector-transfected cells (FIG. 7B). Computer-assisted analysis of the fluorescence intensity/cell area revealed that GRP78/BiP overexpressing cells had a 2.2-fold increase in cell surface TF, compared to wild-type or vector-transfected cells; a result consistent with the increased total TF antigen levels shown in FIG. 6B. Non-specific immunostaining was not observed in cells incubated with normal mouse IgG.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method of inhibiting the generation of active thrombin on the surface of a cell within an atherosclerotic plaque within a mammal, the method comprising increasing the expression or activity of GRP78/BiP, an ER resident calcium-binding protein in said cell by directly administering to said cell a polynucleotide operably linked to a promoter, wherein said polynucleotide encodes GRP78/BiP, whereby said GRP78/BiP is produced in said cell and the generation of active thrombin on the surface of said cell is inhibited.

2. The method of claim 1, wherein said cell is an endothelial cell.

3. The method of claim 1, wherein said cell is a smooth muscle cell.

4. The method of claim 1, wherein said cell is a macrophage.

5. The method of claim 1, wherein said cell is a monocyte.

6. The method of claim 1, wherein the increase in the expression or activity of said GRP78/BiP within said cell results in a decrease in the level of tissue factor procoagulant activity on the surface of said cell.

7. The method of claim 1, wherein said polynucleotide is introduced into said cell using a viral vector.

8. The method of claim 7, wherein said viral vector is an adenoviral vector.

9. The method of claim 1, wherein said polynucleotide is introduced into said cell using a nonviral vector.

10. The method of claim 9, wherein said nonviral vector is introduced into said cell as naked DNA or using liposome-mediated transfection.

* * * * *